United States Patent
Schaefer et al.

(10) Patent No.: US 7,277,744 B2
(45) Date of Patent: Oct. 2, 2007

(54) EARLY DETECTION OF INFLAMMATION AND INFECTION USING INFRARED THERMOGRAPHY

(76) Inventors: Allan L. Schaefer, Box 5451, Lacombe, Alberta (CA) T4L 1X2; Shannon L. Scott, #72, 3725 Victoria Avenue, Brandon, Manitoba (CA) R7B 3C3; Pierre LaCasse, 4 Rue Winder, Lennoxville, Quebec (CA) J1M 1L4; Alan K. W. Tong, 51 Bruns Cresent, Lacombe, Alberta (CA) T4L 1N9

(*) Notice: Subject to any disclaimer, the term of this patent is extended or adjusted under 35 U.S.C. 154(b) by 61 days.

(21) Appl. No.: 10/445,997

(22) Filed: May 27, 2003

(65) Prior Publication Data

US 2004/0019269 A1    Jan. 29, 2004

Related U.S. Application Data

(63) Continuation of application No. 09/533,400, filed on Mar. 22, 2000, now abandoned, which is a continuation-in-part of application No. 09/274,032, filed on Mar. 22, 1999, now abandoned.

(51) Int. Cl.
*A61B 5/01* (2006.01)

(52) U.S. Cl. .................. 600/474; 600/549
(58) Field of Classification Search .......... 600/474, 600/549; 382/128, 131; 374/10, 100, 120, 374/121, 129; 128/922
See application file for complete search history.

(56) References Cited

U.S. PATENT DOCUMENTS

| | | | |
|---|---|---|---|
| 3,335,716 A | | 8/1967 | Alt et al. .................. 600/549 |
| 3,968,774 A | | 7/1976 | Massie |
| 3,989,009 A | | 11/1976 | Robar et al. |
| 4,037,585 A | * | 7/1977 | Gildenberg ................ 378/8 |
| 4,156,179 A | | 5/1979 | Stephen et al. |
| 4,366,381 A | * | 12/1982 | Fischer et al. ........... 250/316.1 |
| 4,403,568 A | | 9/1983 | Fukuhara et al. |
| 4,445,516 A | * | 5/1984 | Wollnik et al. ............ 600/549 |
| 4,548,212 A | * | 10/1985 | Leung .................... 600/549 |
| RE32,758 E | * | 10/1988 | Zartman ................. 600/549 |
| 4,849,885 A | * | 7/1989 | Stillwagon et al. ........ 600/549 |
| 4,865,044 A | * | 9/1989 | Wallace et al. ............ 600/549 |

(Continued)

FOREIGN PATENT DOCUMENTS

DE    195 15 317 A1    10/1996

(Continued)

OTHER PUBLICATIONS

Sandholm et al., "Milk Trypsin-Inhibitor capacity as an indicator of Bovine Mastitis-a Novel Principle which can be Automated", 1984, J. Dairy Research, 51: 1-9.

(Continued)

*Primary Examiner*—Ruth S. Smith
(74) *Attorney, Agent, or Firm*—Greenlee Winner and Sullivan PC

(57) ABSTRACT

The present invention provides a method for the detection of inflammation in animals using infrared thermography. The invention also provides a method for the detection of diseases or disorders that induce inflammation using infrared thermography. The present invention further provides a method for the detection of infections in animals using infrared thermography.

40 Claims, 9 Drawing Sheets

U.S. PATENT DOCUMENTS

| | | | |
|---|---|---|---|
| 5,197,470 A * | 3/1993 | Helfer et al. | 600/342 |
| 5,302,903 A | 4/1994 | De Jong et al. | |
| 5,313,951 A | 5/1994 | Zhao | 600/474 |
| 5,416,417 A | 5/1995 | Peles | |
| 5,458,418 A | 10/1995 | Jones et al. | |
| 5,474,081 A * | 12/1995 | Livingstone et al. | 600/544 |
| 5,474,085 A | 12/1995 | Hurnik et al. | |
| 5,546,955 A * | 8/1996 | Wilk | 600/549 |
| 5,595,444 A | 1/1997 | Tong et al. | |
| 5,637,871 A | 6/1997 | Piety et al. | |
| 5,666,903 A | 9/1997 | Bull et al. | |
| 5,678,566 A | 10/1997 | Dribbon | 600/549 |

FOREIGN PATENT DOCUMENTS

| | | |
|---|---|---|
| WO | WO95/01567 | 1/1995 |
| WO | WO97/14959 | 4/1997 |
| WO | WO98/41860 | 9/1998 |
| WO | WO 98/41860 | 9/1998 |

OTHER PUBLICATIONS

Sisson, S., The Anatomy of the Domestic Animal. W.B. Saunders Comp., Philadelphia. 4$^{th}$ ed. Revised by J.D. Grossman, p. 618, no date available.

Siegmund et al., The Merk Veterinary Manual 4$^{th}$ ed., Merck and Comp. Rathway, N.J., no date available.

Tongel, P. and Mihina, S., "Detection of Mastitis by Means of Electrical Conductivity Measurement", From the Proceedings of the 3$^{rd}$ International Dairy Housing Conference, Orlando, Florida, 1994 p. 257-262.

Turner, A. Tracy., "Thermography", From the Proceedings, 1996, Dubai Symposium.

Nielen, M. et al., "Development of an on-line mastitis detection system within an integrated knowledge-based system for dairy farm management support," 1994, Vet. Research, 25:285-289.

Arnold et al., 1989, "Infra-Red Surface Thermography. Evaluation of a New Radiometry Instrument for Measuring Skin Temperature Over Joints", Clin. Rheumatol. 8:225-230.

Bacon et al., 1976, "Thermography in the Assessment of Inflammatory Arthritis", Clinics in Rheumatic Dis. 2:51-65.

Cena and Clark, 1973, "Thermographic Measurements of the Surface Temperatures of Animals", J. Mammalogy 54:1003-1007.

DeSilva et al., 1986, "Assessment of Inflammation in the Rheumatoid Knee Joint Correlation between Clinical, Radioisotopic, and Thermographic Methods", Ann. Rheum. Dis. 45:277-280.

Devereaux et al., 1985, "Disease Activity Indexes in Rheumatoid Arthritis; a Prospective, Comparative Study with Thermography", Ann. Rheum. Dis. 44:434-437.

Eichel, 1986, "Study of the Temperature Behaviour of the Udder and Teat Skin by Liquid Crystal Thermography", Naturwissenschaftliche Reihe 35:339-345 (in German with English summary).

Esselinckx et al., 1978, "A Thermographic Assessment of Three Intra-Articular Prednisolone Analogues Given in Rheumatoid Synovitis", Br. J. Clin. Pharmacol. 5:447-451.

Fujishima et al., 1994, "Quantitative Evaluation of Postsurgical Inflammation by infrared Radiation Thermometer and Laser Flare-Cell Meter", J. Cataract Refract. Surg. 20:451-454.

Gaughan, 1998, "Thermal Imaging is Gaining Acceptance as a Diagnostic Tool", Biophotonics Intl. Nov./Dec.:48-53.

Hamann, 1985, "Measurement of Machine Milking Induced Teat Tissue Reactions", Milchwissenschaft. 40:16-18.

Hamann and Duck, 1984, "First Results from Measuring the Temperature of Teats Using IR Thermography", Die Milchpraxis 22:148-152 (in German with English translation).

Humik et al., 1984, "Detection of Health Disorders in Dairy Cattle Utilizing a Thermal Infrared Scanning Technique", Can. J. Anim. Sci. 64:1071-1073.

Purohit et al., 1980, "Thermography in the Diagnosis of Inflammatory Processes in the Horse", Am. J. Vet. Res. 41:1167-1174.

Purohit et al., 1980, "Thermographic Diagnosis of Homer's Syndrome in the Horse", Am. J. Vet. Res. 41:1180-1182.

Rajapakse et al., 1981, "Thermography in the Assessment of Peripheral Joint Inflammation—A Re-Evaluation", Rheumatology And Rehabilitation 20:81-87.

Ring, 1975, "Thermography and Rheumatic Diseases", Bibl. Radiol. 6:97-106.

Salisbury et al., 1983, "Heat Distribution Over Normal and Abnormal Joints—Thermal Pattern and Qualification", Ann. Rheumatic Dis. 42:494-499.

Silberstein et al., 1975, "Thermographically Measured Normal Skin Temperature Asymmetry in the Human Male", Cancer 36:1506-1510.

Tsykalo et al., 1982, "Diagnosis of Udder Diseases by the Method of Liquid Crystal Thermography", Veterinariya, Moscow, USSR 7:49-50 (in German with English translation).

Turner, 1983, "Thermographic Evaluation of Horses with Podotrochlosis", Am. J. Vet. Res. 44:535-539.

Vaden et al., 1980, "Thermography: A Technique for Subclinical Diagnosis of Osteoarthritis", Am. J. Vet. Res. 41:1175-1179.

White et al., 1987, "The Use of Infrared Thermography in the Evaluation of Oral Lesions", Int. J. Tiss. Reac. IX:105-114.

Yang and Yang, 1992, "Literature Survey on Biomedical Applications of Thermography", Bio-Medical Materials and Engineering 2:7-18.

Batra, T.R. and McAllister, A.J., "A Comparison of Mastitis Detection Methods in Dairy Cattle", 1984, Canadian J. Anim. Sci. 64: 305-312.

Biagetti, D.R., "Caracteristicas Electricas De La Leche Bovina: Su Utilication Para La Deteccion De La Mastitis", 1992, Rivista-di-Ingegneria Agraria 23: 200-207.

Blood et al., "Mastitis", 1983, Veterinary Medicine 6$^{th}$ ed., Bailliere Tindall, London 15: 451-462.

Clark, J.A. and Cena, K., "Thermographic Measurements of the Surface Temperatures of Animals", 1972, J. of Mammalogy 54:1003-1007.

Cortes et al.,"Clinical and Immunologic Responses of Vaccinated and Unvaccinated Calves to Infection with a Virulent Type-II Isolate of Bovine Viral Diarrhea Virus", 1998. J. Am. Vet. Med. Association 213:1312-1319.

Datta et al., "Real Time Acquisition and Analysis of Milk Conductivity Data", 1984, Transactions of the American Society of Agriculture Engineers 27:1204-1210.

Fang, W. et al., "Mastitis-Causing *Escherichia coli*: Serum Sensitivity and Susceptibility to Selected Antibacterials in Milk", 1995, J. Dairy Sci. 79: 76-82.

Fang W. et al., "A Fluorometric β-Glucuronidase Assay for Analysis of Bacterial Growth in Milk", 1995, Veterinary Microbiology (1995): 361-367.

Fernando et al., "Comparison of Electrical Conductivity of Milk with Other Indirect Methods for Detection of Subclinical Mastitis", 1985, J. Dairy Sci. 68: 449-456.

Jarman et al., "Milk Temperature and Composition Responses to Bacterial Endotoxin", 1986, J. Dairy Sci. 69: (suppl 1.) 178.

Lake et al., "Trials of a Novel Mastitis Sensor on Experimentally Infected Cows", 1991, J. Dairy Sci. 59: 11-19.

Maatjie, K. and Rossing, W., "The Efficacy of In-Line Measurement of Quarter Electrical Conductivity", 1991, Mastitis Newsletter 16: 6-7.

Mattila et al., "Milk Antitrypsin as a Marker of Bovine Mastitis-Correlation with Bacteriology", 1985, J. Dairy Sci. 68:114-122.

Mijnen et al., "The Value of Cell Count, Lactose content, pH and Conductivity of Milk for Mastitis Detection in Individual Cows", 1983, Netherlands Milk and Dairy Journal 37: 65-77.

Nielen et al., "Electrical Conductivity of Milk: Measurement, Modifiers, and Meta Analysis of Mastitis Detection Performance", 1992, J. Dairy Sci. 75: 606-614.

Notsuki et al., "Diagnostic Significance of Variation in Conductivity During Milking", 1983, Proceedings of the World Conference of Animal Production vol. 2., 891-892.

Perdigon, G. et al., "Significance of the Presence of Bovine Milk β-Glucuronidase in Mastitis Detection", 1986, J. Dairy Sci. 69: 27-31.

Rossing et al., "Micro-Electronics in Dairy Herd Management", 1984, Proceedings of th National Conference American Society of Agricultural Engineers, Chicago, 606-613.

Sisson, S., The Anatomy of the Domestic Animal. W.B. Saunders Comp., Philadelphia 4th ed. Revised by J.D. Grossman, p. 618.

Siegmund et al., The Merk Veterinary Manual 4th ed., Merck and Comp. Rathway, N.J.

Ganong, W.F. (1993) *Review of Medical Physiology*, 16th Ed., Appleton and Lang, Norwalk, CT., p. 576.

Hayward, J.A. et al. (1975), "Thermal Balance and Survival Time Prediction of Man in Cold Water," Can J. Physiol. Pharmacol. 53:21-32.

Lamarque, J. et al. (1975), "Etude Thermographique Expérimentale en Pathologie Artérielle Périphérique," Ann. Radiol. 18:513-523.

Van der Laken, C.J. et al. (1998), "Scintigraphic detection of infection and inflammation: new developments with special emphasis on receptor interaction," Eur. J. Nucl. Med. 25:535-546.

* cited by examiner

EARLY DETECTION OF INFLAMMATION AND INFECTION USING INFRARED THERMOGRAPHY

This is a continuation of U.S. patent application Ser. No. 09/533,400, filed Mar. 22, 2000, now abandoned, which in turn is a continuation-in-part of U.S. patent application Ser. No. 09/274,032, filed Mar. 22, 1999, now abandoned, both of which are incorporated herein by reference in their entirety.

1. FIELD OF THE INVENTION

The invention relates to the use of infrared thermography imaging in animals for the early detection of inflammation. The invention further relates to the use of infrared thermography in animals for the early detection of infection.

2. BACKGROUND OF THE INVENTION

Inflammation plays a fundamental role in host defenses and the progression of immune-mediated diseases. The inflammatory response is initiated in response to tissue injury (e.g., trauma, ischemia, and foreign particles) and infection by a complex cascade of events, including chemical mediators (e.g., cytokines and prostaglandins) and inflammatory cells (e.g., leukocytes). The inflammatory response is characterized by increased blood flow, increased capillary permeability, and the influx of phagocytic cells. These events result in swelling, redness, warmth (altered heat patterns), and pus formation at the site of injury.

A delicate well-balanced interplay between the humoral and cellular immune elements in the inflammatory response enables the elimination of harmful agents and the initiation of the repair of damaged tissue. When this delicately balanced interplay is disrupted, the inflammatory response may result in considerable damage to normal tissue of uncontrolled inflammatory responses, clinical intervention is needed to prevent tissue damage and organ dysfunction. Diseases such as Rheumatoid Arthritis, Osteoarthritis, Crohn's disease, psoriasis, or inflammatory bowel disease, are characterized by chronic inflammation.

Early detection and localization of inflammation is a critical step in the implementation of appropriate treatment of a subject. However, non-invasive techniques for the detection of inflammation remain elusive. A variety of techniques including computed tomography (CT), magnetic resonance imaging (MRI), ultrasonography, and scintigraphic imaging are used to attempt to image secondary effects of markers of inflammation. However, CT, MRI, and ultrasonography rely on anatomical changes that result from inflammation, which occur late in the inflammatory response (van der Laken, C. J., et al., 1998, European Journal of Nuclear Medicine 25: 535-546). Therefore, these techniques are not useful for detecting the early phase in the development of inflammation. Scintigraphic imaging is a non-invasive method of scanning the entire body using radiopharmaceuticals (e.g., radiolabeled receptor-specific small proteins and peptides), which specifically bind to receptors abundant in the area of inflammation. The use of radiopharmaceuticals for imaging inflammation is limiting because it requires: (i) that the radiopharmaceutical specifically interacts with its receptor; (ii) that the radiopharmaceutical has a high affinity for its receptor; (iii) that the radiopharmaceutical specifically localizes to the site of inflammation, which is dependent on the receptor expression in the inflammatory response; (iv) that the receptor is accessible to the radiopharmaceutical; (v) that the radiopharmaceutical has high and early uptake; (vi) that the radiopharmaceutical is rapidly cleared; (vii) that the radiopharmaceutical does not accumulate in non-targeted tissues and result in high background; and (viii) that the radiopharmaceutical is not toxic (van der Laken, C. J., et al., 1998, European Journal of Nuclear Medicine 25: 535-546). The induction of a biological response by a radiopharmaceutical is a major drawback of using scintigraphic imaging. In addition to these technologies, inflammation may also be detected by feeling or visual observance of the site of injury or pain. However, this method is only useful for detecting the late stages in the development of inflammation.

The inability to diagnose and image inflammation in vivo continues to be a major obstacle to the successful treatment of inflammatory disorders. Currently, the only viable method for diagnosing inflammatory disorders, such as fibrosis, is by biopsy. This method is invasive and often results in an amount of healthy tissue being removed along with the tissue suspected of being affected by inflammation. Therefore, a great need exists for an accurate, non-invasive, rapid, and inexpensive method for detecting inflammation.

2.1. Infectious Diseases

Viral and bacterial infections typically result in the development of local or systemic inflammation and catabolism of tissues at the site of infection. The inflammatory response to an infection whether acute or chronic is often tissue or organ centered and as such is characterized by increased blood flow and white blood cell activity (i.e., phagocytic cell activity) in affected areas. The appearance of localized welling, discoloration and tissue debris are often apparent and significant tissue damage can result.

Early detection of viral and bacterial infections is important not only for the implementation of appropriate treatment of a subject but also for the prevention of the spread of the infections. A variety of methods are available for the detection and clinical diagnosis of viral and bacterial infections, including immunologic methods, which detect the presence of viral or microbial antigens or antibodies specific to a virus or microbe. A variety of immunological assays are available for detecting viral or microbial antigens or antibodies specific to a virus or microbe, including ELISAs (enzyme linked immunosorbent assays), solid-state radioimmunoassays, and immunofluorescent assays. However, immunological assays for detecting viral or bacterial infections require a laboratory and someone with technical expertise to perform the assays. Further, the biological samples required to perform immunological assays are not easily obtained from an animal. Additionally, the immunological assays are too costly for individual or sporadic infections and are generally not performed until clinical symptoms have manifested. Therefore, a need exists for a simple, rapid, non-invasive and inexpensive diagnostic technique for the early detection of viral and microbial infections.

2.2 Mastitis

Mastitis is an inflammation of the mammary gland normally caused by a bacterial or mycotic pathogen. The disease is of great concern in the dairy industry, where significant economic loss can occur due to the requirement to not use the affected milk for human consumption and due to the shortened milking life of the affected animals. The etiology of the disease is well described in the literature pertaining to this topic, e.g., see, Siegmund et al., 1973, The Merk Veterinary Manual 4$^{th}$ ed., Merck and Comp. Rathway, N.J.; Blood et al., 1983, Veterinary Medicine 6$^{th}$ ed., Bailliere Tindall, London.

The successful treatment of mastitis is possible using a variety of animal management, milking hygiene and antibiotic agents. However, given the expense and labour for the treatment of mastitis, treatment is usually not initiated until the condition is diagnosed clinically.

Numerous mastitis tests have also been proposed, including most recently the use of electrical conductivity of the milk (Notsuki et al., 1983, Proceedings of the World Conference on Animal Production Vol 2., 891-892; Datta et al., 1984, Transactions of the American Society of Agriculture Engineers 27:1204-1210; Batra, T. R. and McAllister, A. J., 1984, Canadian J. Anim. Sci. 64:305-312; Maatje, K. and Rossing, W., 1991, Mastitis Newsletter 16:6-7; Lake et al., 1991, J. Dairy Sci. 59:11-19; Biagetti, D. R., 1992, Rivista-di-Ingegneria Agraria 23:200-207; Nielsen et al., 1992, J of Dairy Sci. 75: 606-614; Tongel et al., 1994, Proceedings 3$^{rd}$ International Dairy Housing Conference, Orlando, Fla., 257-262). In addition to electrical conductivity, the use of milk components have been suggested as good indicators of mastitis, including such elements as sodium, chloride, potassium, lactose and bovine serum albumin (BSA) (Fernando et al., 1985, J. Dairy Sci. 68: 449-456), milk temperature (Datta et al., 1984, Transactions of the American Society of Agriculture Engineers 27:1204-1210; Rossing et al., 1984, Proceedings of the National Conference American Society of Agricultural Engineers, Chicago, 606-613; Jarman et al., 1986, J. Dairy Sci. 69:(suppl 1.) 178), milk pH (Mijnen et al., 1983, Netherlands Milk and Dairy Journal 37:65-77), milk anti-trypsin (Mattila et al., 1985, J. Dairy Sci. 68:114-122) as well as general milking information such as volume or yield (Nielsen et al., 1994, Veterinary Research 25:285-289). Numerous patents have been issued describing the methods of mastitis detection, particularly for the use of electrodes or a variety of electrical conductivity tests for milk (U.S. Pat. No. 3,989,009; U.S. Pat. No. 3,968,774; U.S. Pat. No. 4,156,179; Australian Patent Application AU A178 553/81; U.S. Pat. No. 5,302,903; U.S. Pat. No. 5,416,417).

All of these aforementioned procedures can be useful. However, none are particularly effective at early detection (e.g., within the first few hours) of mastitis onset and, as described by Batra and McAllister (1984), these aforementioned procedures often have an unacceptably high percentage of false negatives (i.e., failure to identify an infected cow). For example, electrical conductivity is reported to have a 29.4% false negative value and is also shown to be unreliable unless selective milk samples are used (Noksuki et al., 1983, Proceedings of the World Conference on Animal Production Vol 2., 891-892).

Mastitis is currently detected predominantly by the use of inflammatory tests such as the "Wisconsin Mastitis Test" or CMT, which as described by Siegmund (1973, page 817) is a rather time consuming laboratory type diagnostic method which will indicate the relative leukocyte or somatic cell count in the milk of cows suspected of having mastitis. Unfortunately, these types of tests are not particularly effective in detecting the earliest onset or subclinical cases of mastitis. Furthermore, the need to capture the animal and collect milk samples complicates the use of this method. These factors are important in that the earlier the mastitis condition can be detected, the earlier treatments can begin and the higher the likelihood of successful treatment in a shorter period of time.

As mentioned previously, these tests have in common the requirement of collecting and analyzing milk samples from animals suspected of having mastitis. Clinical diagnosis of the infected animal is also routinely conducted. However, clinical signs of mastitis usually do not occur until the animal has progressed well into the disease state. Furthermore, some diagnostic tools, such as rectal temperature, while usually efficacious, are often not as sensitive as would be desired or are simply impractical. Again, it should be noted that the earlier a diagnosis can be performed, the earlier treatment can be initiated, which results in a lower treatment cost and a more successful outcome. Therefore, there remains a need for an accurate, inexpensive, non-invasive, rapid method for predicting early mastitis onset in dairy animals.

2.3. Bovine Viral Diarrhea

Bovine virus diarrhea (BVD) virus is a pestivirus that is characterized by erosions and hemorrhages of the alimentary tract (Siegmund, O. H., 1973, The Merck Veterinary Manual. Merck and Co. Inc. Rathway, N.J.; and Blood et al., 1983, Veterinary Medicine. Baillere. Tindall, London). Type 1 and type 2 strains as well as subgroups of BVD virus have been identified. Animals infected with BVD virus typically exhibit anorectic conditions, rumen stasis, temperature elevations and diarrhea between days 4 and 10 postinfection. Type 2 BVD virus is associated with higher levels of gastrointestinal tract hemorrhage, morbidity and mortality than type 1BVD virus.

BVD is readily transmitted by oral contact and is present in the bovine populations of most countries. BVD is a significant problem in North American cattle populations, causing high morbidity and mortality especially in veal, dairy and beef populations (Cortese et al., 1998, J. Am. Vet. Med. Association 213: 1312-1319). Further, the ability to obtain a reliable vaccine has remained elusive (Cortese et al., 1998, supra).

BVD is currently detected and diagnosed by immunological assays such as serum neutralization assays and serum immuno-diffusion assays. A clinical scoring test is also frequently used to describe or rank the severity of the disease progression and symptoms (see, e.g., Blood et al., 1983, supra; and Cortese et al., 1998, supra). The immunological assays are laborious, time consuming and expensive, and require the collection of a biological sample. Thus, there remains a need for an inexpensive, non-invasive, accurate and rapid method for the detection of an infectious disease such as BVD.

2.4. Infrared Thermography

Infrared thermography is a non-invasive technique that enables temperatures to be monitored and recorded. Unsuccessful attempts have been made to use infrared thermography in human medicine as a diagnostic aid for a variety of conditions, such as tumor detection and cardiovascular disease (Clark, J. A. and Cena, K., 1972, J. of Mammalogy 54:1003-1007). Infrared thermography has been attempted in veterinary medicine to detect and diagnosis a variety of conditions, such as podotrochlosis in horses (Tumer, T. A., 1983, Am. J. Vet. Res. 44:535-539) and clinical damage in an udder (Tsykalo, A. L. et al., 1982, USSR (7):49-50).

The early infrared thermography detection systems were bulky, complex, and required frequent recharging with liquid nitrogen. Furthermore, the spatial resolution was poor, the exposure time was long, and the minimum resolvable temperature difference was large for the infrared thermography systems. Reliable detection of inflammation was not achieved. In addition, many physicians and veterinarians were not adequately trained to interpret the data from the infrared imagery and there was a high false positive rate. Thus, the infrared thermography was branded as a failure and has not been explored much by the medical or veterinary communities for the past three decades.

3. SUMMARY OF THE INVENTION

The present invention provides a method using infrared thermography for the detection of inflammation in animals. The invention also provides a method using infrared thermography for the diagnosis of diseases or disorders that induce inflammation such as inflammatory disorders, allergies, and viral or bacterial infection. The invention further provides a method using infrared thermography for the detection of an infection in an animal. In particular, the present invention provides for the detection of an infection in an animal by measuring temperature changes resulting from the animal's immune response to the infection using infrared thermography. The catabolism of tissue and the inflammatory response induced in response to an infection in an animal both generate temperature changes which can be measured using infrared thermography.

The present invention is based, in part, on the surprising discovery that temperature differences less than 1° C. are clinically significant. This discovery was made possible by employing induction models of mastitis and BVD that allowed the Applicants to evaluate inflammation or infection resulting from known etiologies and to compare the infrared characteristics obtained using an infrared camera with outcomes obtained with other diagnostic procedures. Accordingly, Applicants' discovered that temperature differences less than 1° C. indicate early or subclinical inflammation or infection, and that temperature differences greater than 1° C. indicate later stages of development of inflammation or clinical infection.

4. DESCRIPTION OF THE FIGURES

5. DETAILED DESCRIPTION OF THE INVENTION

Figure 1:
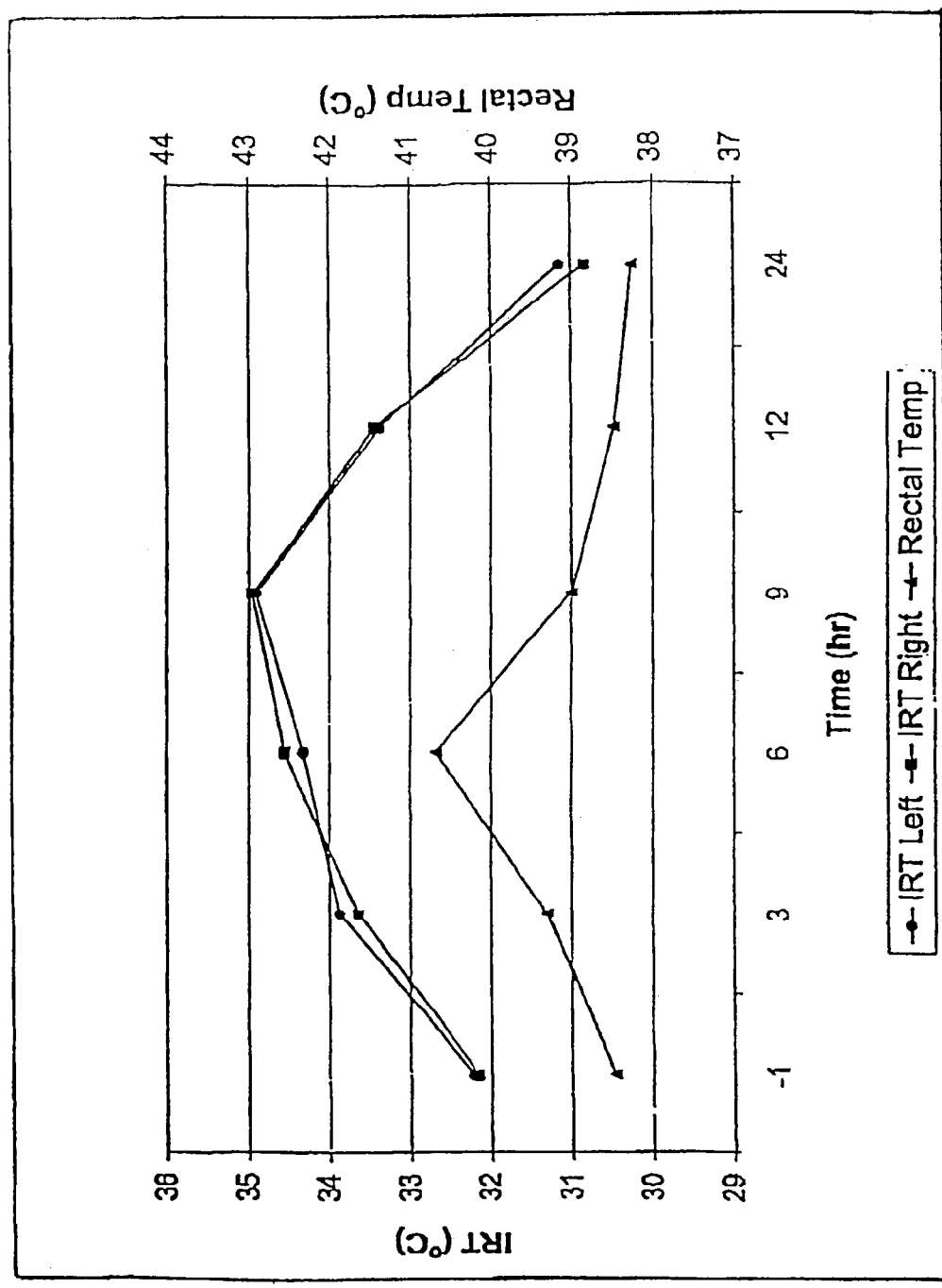
FIG. 1 is a graph of rectal temperature and udder infrared thermography values for milking dairy cows having mastitis induced in the left distal quadrant (n=20). Data for both the left and right distal quarters of the udder are shown.

The present invention relates to the use of infrared thermography for the early or subclinical detection of inflammation in animals. The present invention also relates to the use of infrared thermography in the diagnosis of diseases or disorders that induce inflammation and/or induce the catabolism of tissues. The present invention provides methods for detecting inflammation of an anatomical structure of an animal, preferably a mammal and more preferably a non-human animal. The present invention further provides methods for detecting infection of an anatomical structure of an animal, preferably a mammal. In one embodiment, the present invention provides methods for detecting infection of an anatomical structure in a non-human animal. In yet another embodiment, the present invention provides methods for detecting infection in humans. The term "anatomical structure" used herein refers to any definable area of an animal, preferably a tissue or a joint of an animal, that radiates infrared energy and which may or may not be symmetrical.

The invention provides methods for detecting inflammation of all anatomical structures of animals, except the joints. The present invention also provides methods for detecting inflammation of the joints of all mammals, except humans. The invention also provides methods for detecting inflammation or infection in all non-human mammals, including but not limited to pigs, horses, cows (e.g., *Bos taurus* and *Bos indicus*), dogs and cats. The present invention also provides methods for detecting local or systemic infection in animals, preferably a mammals. Further, the present invention also provides methods for detecting acute or chronic infection in animals, preferably a mammals.

The invention provides a method for detecting inflammation of an anatomical structure of an animal, comprising the following steps: (i) obtaining an infrared thermographic image of an anatomical structure of an animal; (ii) determining the mean temperature of the infrared thermographic image; and (iii) detecting early or subclinical inflammation of an anatomical structure of an animal if there is a change in the mean temperature of less than 1° C. of an anatomical structure relative to the mean temperature of the same anatomical structure of the same animal or a population of animals of the same species obtained from infrared thermographic images taken when there was no inflammation of the anatomical structure. The term "subclinical" as used herein refers to inflammation of an anatomical structure of an animal that has not manifested itself clinically.

The invention also provides a method for detecting inflammation of an anatomical structure of an animal, comprising the following steps: (i) obtaining an infrared thermographic image of an anatomical structure of an animal; (ii) determining the mean temperature of the infrared thermographic image; and (iii) detecting late stage development of inflammation of an anatomical structure of an animal if there is a change in the mean temperature of greater than 1° C. of an anatomical structure relative to the infrared thermographic image; and (iii) detecting the successful treatment of inflammation of the anatomical structure by comparing the mean temperature of the anatomical structure with the mean temperature of the same anatomical structure obtained from the same animal or a population of animals of the species when healthy.

The present invention also provides a method for detecting an infection in animal comprising the following steps: (i) obtaining an infrared thermographic image of the anatomical structure or a portion thereof of the animal; and (ii) detecting early or subclinical infection of said animal if there is a change in the mean temperature of less than 1° C. relative to the mean temperature of the same anatomical structure in the same animal pre-infection or relative to the mean temperature of the same anatomical structure in a population of uninfected animals of the same species, background and class. In preferred embodiments of the present invention, the anatomical structure of an animal imaged to detect infection is the eye or the nose (i.e., a sinus).

The present invention also provides a method for detecting an infection in an animal comprising the following steps: (i) obtaining an infrared thermographic image of the anatomical structure or a portion thereof of the animal; and (ii) detecting clinical infection of said animal if there is a change in the mean temperature of greater than 1° C. relative to the mean temperature of the same anatomical structure in the same animal pre-infection or relative to the mean temperature of the same anatomical structure in a population of uninfected animals of the same species, background and class.

The present invention also provides a method for detecting when a clinical treatment for treating an infection in an animal was successful, comprising the following steps: (i) obtaining an infrared thermographic image of the anatomical structure of the animal; and (ii) detecting the successful treatment of the infection by comparing the mean temperature of the anatomical structure of the animal to the mean temperature of the same anatomical structure of the same animal preinfection or a population of uninfected animals of the same species.

The present invention provides a method for detecting a local infection of an anatomical structure of an animal, comprising the following steps: (i) obtaining an infrared thermographic image of an anatomical structure of an animal; (ii) obtaining an infrared thermographic image of the symmetrical anatomical structure of the animal; (iii) determining the total temperature of the infrared thermographic images for the symmetrical anatomical structures; and (iv) detecting a local infection of an anatomical structure if the total temperature of the symmetrical anatomical structures differ by greater than a predetermined amount.

The invention also provides a method for detecting a local infection of an anatomical structure of an animal, comprising the following steps: (i) obtaining an infrared thermographic image of the anatomical structure of an animal; (ii) obtaining an infrared thermographic image of the symmetrical anatomical structure of the animal; (iii) comparing the infrared thermographic image obtained to an infrared thermographic image of the symmetrical anatomical structure of the animal; and (iv) detecting infection of the anatomical structure of the animal if there is a relative difference in the temperature between the anatomical structure and the symmetrical anatomical structure of the animal.

5.1 Induction Model of Mastitis

The present invention is based upon the surprising discovery that temperature differences less than 1° C. are clinically significant. This discovery was made possible, in part, by employing an induction model of mastitis, which displays a known etiology, such that infrared thermal expression could be compared to known outcomes. The use of the induction model has many advantages including: (i) the inflammatory agent is known both in quantitative and qualitative terms; (ii) the exact time of the onset of inflammation is known; and (iii) the exact stage or progression of the inflammation is known. Furthermore, due to the unique anatomy of the udder of a cow, the progression of an infected quarter can be compared to a non-infected quarter. The udder of a dairy cow is unique in that all four quarters are essentially independent in terms of their vascular supply (Sisson, S., The Anatomy of the Domestic Animal. W.B. Saunders Comp., Philadelphia. $4^{th}$ ed. Revised by J. D. Grossman, page 618), such that inflammation induced in one quarter of the udder through the use of a mastitis induction model does not affect any other quarter of the udder. Hence, the animal can act as its own control. Briefly, in achieving the invention, one quarter of the udder of a test population of lactating dairy cattle was infected with *Escherichia coli* (*E. coli*) endotoxin and the time course of the resulting inflammation was followed for several days using a variety of analytical tools, including infrared thermography. Over a 72 hour time course, milk samples were obtained from the left (induced) and right (non-induced) distal (hind) quarters of the udder and analyzed for objective indicators of inflammation by conventional analytical procedures. Contemporaneously with the milk samples, infrared thermographic images of the cows were obtained, so that the infrared thermal expression of the animal could be monitored over the course of the induced inflammation.

It was found that within hours after induction of inflammation, significant changes in the thermal expression of the cows could be detected with infrared thermography. This was surprising, in that, as discussed previously, conventional thought would dictate that any temperature changes occurring in subclinical cases of mastitis would be too subtle to detect. Moreover, these changes in thermal expression were observed in all cows in which inflammation was induced, indicating that altered thermal expression, as detected by infrared thermography, is a reliable indicator of inflammation. Significant changes in infrared thermal expression included: (i) a temperature increase; (ii) a more rapid rate of temperature change; and (iii) swelling of the affected quarter of the udder, resulting in a reduction in the symmetry of the thermal expression between the udder quarters with the affected quarter being both hotter and larger. In the present invention, one or more of these changes, detected by infrared thermography, is used to diagnose inflammation.

In one embodiment of the present invention, mastitis in a mammal is detected by: (i) obtaining an infrared thermographic image of a mammary gland of said mammal, said infrared thermographic image providing temperature information about said mammary gland; and, (ii) identifying said mammal as having a high probability of having mastitis if a measure of said temperature information is greater than a predetermined value by at least a predetermined amount. In another embodiment of the present invention, mastitis in a mammal having an udder is detected by: (i) obtaining an infrared thermographic image of one quarter of the udder of said mammal at time 0, said infrared thermographic image providing temperature information about said udder quarter of said mammal; (ii) obtaining an infrared thermographic image of the same quarter of the udder of said mammal at a later time, said infrared thermographic image providing temperature information about said udder of said mammal; (iii) determining a total temperature for a first image, said first image corresponding to said quarter of the udder of said mammal at time 0; (iv) determining a total temperature for a second image, said second image corresponding to said quarter of the udder of said mammal at a later time; and (v) identifying said mammal as having a high probability of having mastitis if the total temperature for said first image differs from the total temperature for said second image by greater than a predetermined amount. In yet another embodiment of the present invention, mastitis in a mammal having an udder is detected by: (i) obtaining images of the two frontal quarters or two rear quarters of the udder of said mammal; (ii) determining the total temperature of a first image, said first image corresponding to one frontal quarter or one rear quarter of the udder of said mammal; (iii) determining the total temperature of a second image, said second image corresponding to the other frontal quarter or the other rear quarter of the udder of said mammal; and (iv) identifying said mammal as having a high probability of having mastitis if the total temperature of said first image differs from the total temperature of said second image by greater than a predetermined amount.

5.2. Induction Model of BVD Virus Type 2

The present invention is based, in part, on the surprising discovery that mean temperatures less than 1° C. obtained using infrared thermography are indicative of an infection. This discovery was made possible by employing an induction model of a viral infection displaying a known etiology such that infrared thermographic expression could be compared to known outcomes.

Briefly, a population of BVD and infectious respiratory disease (IBR) seronegative calves were infected intranasally with BVD type 2 virus ($2\times10^7$ $TCID_{50}$ of type 2 strain 24515) and the time course of the resulting infection was followed for approximately three weeks. A variety of laboratory tests and clinical scoring procedures were used including infrared thermography. In addition, a group of contemporary, uninfected calves were studied simultaneously. Biological samples (i.e., blood and saliva samples) and infrared images were obtained from infected and uninfected calves about every second day postinfection.

Statistically significant changes in the mean temperature of anatomical structures (e.g., the eye and nose) of BVD virus infected animals were detected using infrared thermography as early as 1 day post-infection and that such changes were often of magnitudes less than 1° C. Further, the BVD virus infection was detected using infrared thermography several days to one week before it was detected using laboratory tests for objective measurements of, for example, acute phase proteins such as haptoglobin, and before it was detected using conventional clinical scores.

In one embodiment of the present invention, infection in an animal is detected by: (i) obtaining an infrared thermographic image of an anatomical structure of said animal, said infrared thermographic image providing temperature information about said anatomical structure; and (ii) identifying said animal as having a high probability of having an infection if a measure of said temperature information is greater than a predetermined value by at least a predetermined amount. In another embodiment of the present invention, infection in an animal is detected by: (i) obtaining an infrared thermographic image of an anatomical structure of said animal, said infrared thermographic image providing temperature information about said anatomical structure; (ii) obtaining an infrared thermographic image of the same anatomical structure of an uninfected animal or a population of uninfected animals, said infrared thermographic image(s) providing temperature information about said anatomical structure; and (ii) identifying the animal in step (i) as having a high probability of having an infection if a measure of the temperature information in step (i) is greater than the temperature information in step (ii).

5.3. Infrared Thermographic Camera capturing reliable infrared data from live animals is a technical and operational challenge. Moving conscious animals to designated analytical or assessment rooms where equipment, monitors and data collection are fixed permanently, is not always possible. In fact, handling and management procedures by themselves can be stressful to animals resulting in non-steady state or aberrant temperature profiles. Hence, the animal technician or camera operator is often required to move to the animal's environment. Therefore, utilizing a user friendly infrared camera that is installed in the animal's environment or that is portable is an advantage when capturing infrared data from live animals.

In one embodiment of the invention, the infrared thermographic camera is held and operated with one hand, which is a significant advantage when obtaining infrared thermographic images of an anatomical structure of animals. In a preferred embodiment, the portable, hand held camera is light enough to be managed easily. In another embodiment, the infrared thermographic camera is installed in the animal's environment (e.g., a barn). In another preferred embodiment of the invention, the infrared thermographic camera: (i) is designed to operate and function optimally within the range of temperatures normally anticipated in animals displaying inflammation (25° C. to 35° C.) without recalibration; (ii) is capable of resolving temperature differences of less than 1° C.; (iii) has a lens focal length that is optimal for use in closer ranges with animals (e.g., focal length=6 centimeters to infinity); (iv) has a wavelength range of 5 to 14 μm; (v) is encased in a hardened, water resistant case, which is compatible for the capture of data in animal environments; (vi) has a flip out display for accurate viewing of the image; and (vii) is capable of compact data storage in the instrument and/or linkage to peripheral monitors. In the examples described, the Inframetrics 760 broadband camera (Inframetrics Co. North Billercia, Mass.) was used to obtain the infrared thermographic images.

5.4. Protocol for Infrared Thermographic Imaging

For predicting the early onset of inflammation, each animal or animals suspected of presenting inflammation in a population are scanned from about 1-3 meters away. For detection of inflammation due to mastitis, the preferred range is 175 cm. Infrared thermographic images of all non-human animals are collected preferentially from the distal (hind) view showing a clear display of the back two quarters. However, other images such as the ventral or lateral view would also have utility.

Environmental factors such as motion, extraneous radiant energy, and ambient temperature must be controlled when using infrared thermography to detect inflammation. Motion, for example, can be controlled by immobilizing the animal (e.g., a cow can be tied with a neck chain). Preferably, the animals should be at rest when the infrared images are obtained and should not be experiencing the thermal effects resulting from the digestion of food when the infrared images are obtained. Infrared thermographic images should be obtained under cover and shielded from the sun. Preferably, the ambient temperature of the environment should be within the animals thermal neutral zone, which is typically between 20° C. and 30° C. Artifacts such as debris on the surface of the animal, scar tissue, irregular patterns of hair length, liniment and wraps should be eliminated to avoid interference with the infrared thermographic image(s). The animal also should be acclimated to the site of the examination for at least ten minutes prior to the examination. In a preferred embodiment, the infrared images should be obtained at the same time of day such that circadian and diurnal rhythm is taken into account.

5.5. Interpretation of Infrared Thermographic Images

The thermal expression of an animal is determined by obtaining infrared thermographic images. As used herein, the term "infrared thermographic image" is meant to include a scan output in the form of either or both a visual image and corresponding thermal or temperature data. The output from infrared cameras used for infrared thermography typically provides an image comprising a plurality of pixel data points, each pixel providing a temperature data point that can be further processed by computer software to generate, for example, mean temperature for the image, or for a discrete area of the image, by averaging the data points over the number of pixels.

It will be appreciated by those of skill in the art that an infrared thermographic image, comprising a plurality of pixels, provides a large number of temperature data points. Therefore, before comparing the temperature information to a predetermined value, determining a rate of temperature change, or determining a difference in total temperature, it is useful to obtain some measure that is representative of the entirety of the temperature information provided by an infrared thermographic image or a part thereof. Selected measures for the temperature information derived from each infrared thermographic image for the subject animal are determined by statistical techniques known in the art. Preferred measures include measures of central tendency, measures of dispersion, and measures of total temperature.

The term "measure of central tendency" as used herein is a statistical measure of a point near the center of a group of data points; without limitation, the term includes the mean, median, and mode. The term "measure of dispersion" as used herein is meant to include statistical measures of spread from the measure of central tendency for the group, and include, without limitation, variance, standard deviation and coefficient of variation. Definitions of these statistical terms may be found in standard statistics texts, such as Steel and Torrie (1960) R. G. D. Steel and J. H. Torrie, McGraw Hill Company, Inc., NY, which definitions are incorporated herein by reference. As used herein, the term "total temperature" means a measure of the central tendency for the temperature information from an infrared thermographic image×image area or image volume expressed in pixels (e.g., if the mean temperature=20° C. and the image is equal to 200 pixels, then the total temperature=20° C.×200 pixels=4000 pixels).

An uncalibrated, digitized thermographic image may consist of, for example, 135×256 pixels. In analyzing the thermographic image, the relative radiant surface temperature represented by each pixel of the uncalibrated image may be represented by assigning each pixel a numerical value in the range from, for instance, 0 to 255. The pixel values are mapped to actual Celsius temperature by relating them to the maximum and minimum temperature settings of the infrared camera through the following formula:

$$\text{Actual Temperature} = \frac{(\text{max temp setting} - \text{min temp setting}) \times \text{pixel value}}{256}$$

To assist a human operator in viewing the infrared thermographic images on a computer monitor, pseudo colours can be generated by assigning a specific colour to all pixels with temperature values within a certain range.

The entire thermographic image may be processed. In a preferred embodiment, only data for a part of the image corresponding to the area of interest of the animal is analyzed. Known computer analysis procedures, such as planometry, can be used to restrict the image analysis to the selected area of interest of the animal (e.g., a fixed "box" area can be applied around the eyes for a group of animals of interest). For each infrared thermographic image obtained for an animal, the image area and the selected image temperature statistics are calculated. Selected statistical measures of the temperature information (each pixel in the infrared thermographic image providing a temperature data point), such as the mean, median, mode, standard deviation, variance, and coefficient of variation can be determined by well-known statistical techniques such as those described by Steel and Torrie (1980). Suitable software for analyzing the thermographic images include Thermogram™ image software (Inframetrics, Inc,. North Billercia, Mass.) and Viewscan™ Software (Viewscan Ltd., Concord, ON.). Mathematical models using such analytical approaches as neural nets can also utilized to analyze the thermographic image.

In one embodiment of the present invention, temperature differences between symmetrical anatomical structures are compared to detect inflammation. For example, the lack of symmetry between affected and non-affected quarters of an cow's udder can be used to detect mastitis. In a preferred embodiment, the area or volume information is combined with the infrared thermographic temperature to better discern the lack of symmetry between the affected and the non-affected anatomical structure. The area or volume represented by selected portions of the infrared thermographic images can be determined by known techniques.

In an embodiment of the present invention, inflammation of an anatomical structure of an animal is detected if a measure of temperature information for an infrared thermographic image of an anatomical structure of the animal differs by at least a predetermined amount or a statistically significant amount from a predetermined value. In another embodiment of the present invention, infection in an animal can is detected if a measure of temperature information of an anatomical structure differs by at least a predetermined amount or a statistically significant amount from a predetermined value. The predetermined value may represent published conventional temperature data representing animals of the same species as the subject animal, which can be adjusted to reflect infrared thermographic temperature values. Alternatively, the predetermined value may be an arbitrary value, the value having been determined through trial and error to be useful for detecting inflammation or infection of an anatomical structure of an animal. Preferably, the predetermined value represents an equivalent measure of temperature information for infrared thermographic images of the particular anatomical structure obtained for members of a population of the same species of animal being examined when there was no inflammation or infection of the anatomical structure. More preferably, the predetermined value represents an equivalent measure of temperature information for one or more infrared thermographic images of the animal mean temperature of the same anatomical structure of the same animal or a population of animals of the same species obtained from infrared thermographic images taken when there was no inflammation of the anatomical structure.

The invention also provides a method for detecting inflammation of an anatomical structure of an animal, comprising the following steps: (i) obtaining an infrared thermographic image of an anatomical structure of an animal after an event; (ii) comparing the infrared thermographic image obtained to infrared thermographic images of the same anatomical structure of the same animal or a population of animals of the same species prior to the event; and (iii) detecting inflammation of the anatomical structure of the animal if there is a relative difference in the temperature of the anatomical structure of the animal. The term "event" as used herein refers to any activity that may result in inflammation of an anatomical structure of an animal, including surgery.

The present invention provides a method for detecting inflammation of an anatomical structure of an animal, comprising the following steps: (i) obtaining an infrared thermographic image of an anatomical structure of an animal; (ii) obtaining an infrared thermographic image of the symmetrical anatomical structure of the animal; (iii) determining the total temperature of the infrared thermographic images for the symmetrical anatomical structures; and (iv) detecting inflammation of an anatomical structure if the total temperature of the symmetrical anatomical structures differ by greater than a predetermined amount. The term "symmetrical anatomical structure" as used herein refers to an anatomical structure that has symmetry to another anatomical structure of an animal (e.g., one leg compared to another leg of an animal).

The invention also provides a method for detecting inflammation of an anatomical structure of an animal, comprising the following steps: (i) obtaining an infrared thermographic image of the anatomical structure of an animal; (ii) obtaining an infrared thermographic image of the symmetrical anatomical structure of the animal; (iii) comparing the infrared thermographic image obtained to an infrared thermographic image of the symmetrical anatomical structure of the animal; and (iv) detecting inflammation of the anatomical structure of the animal if there is a relative difference in the temperature between the anatomical structure and the symmetrical anatomical structure of the animal.

The present invention also provides a method for detecting when a clinical treatment for treating inflammation of an anatomical structure of an animal was successful, comprising the following steps: (i) obtaining an infrared thermographic image of the anatomical structure of the animal; (ii) determining the mean temperature of the obtained at a time when there was no inflammation or infection of the anatomical structure of the animal, and more preferably, when the animal was healthy.

In a preferred embodiment, a change in the mean temperature of less than 1° C. of an anatomical structure relative to the mean temperature of the same anatomical structure of the same animal or a population of animals of the same species obtained from infrared thermographic images taken when there was no inflammation of the anatomical structure indicates early or subclinical inflammation. In another preferred embodiment, a change in the mean temperature of greater than 1° C. of an anatomical structure relative to the mean temperature of the same anatomical structure of the same animal or a population of animals of the same species obtained from infrared thermographic images indicates late stage development of inflammation. In another preferred embodiment, inflammation of an anatomical structure of an animal is detected if the mean of the temperature information obtained from the infrared thermographic image is preferably greater than 0.2° C., more preferably greater than 0.1° C. the mean of the temperature information for previously obtained infrared thermographic images of the same animal when there was no inflammation of the anatomical structure. In yet another preferred embodiment, inflammation of an anatomical structure of an animal is detected if the mean of the temperature information obtained from the infrared thermographic image is preferably greater than 0.2° C., more preferably greater than 0.1° C. the mean temperature obtained from infrared thermographic images for the same anatomical structure of the same species of animal when there was no inflammation of the anatomical structure.

In a preferred embodiment, a change in the mean temperature of less than 1° C. of an anatomical structure relative to the mean temperature of the same anatomical structure of the same animal preinfection indicates early or subclinical infection. In a preferred embodiment, a change in the mean temperature of less than 1° C. of an anatomical structure relative to the mean temperature of the same anatomical structure of one or more uninfected animals of the same species indicates early or subclinical infection. In a preferred embodiment, a change in the mean temperature greater than 1° C. of an anatomical structure relative to the mean temperature of the same anatomical structure of the same animal preinfection indicates clinical infection. In yet another preferred embodiment, a change in the mean temperature greater than 1° C. of an anatomical structure relative to the mean temperature of the same anatomical structure of one or more uninfected animals of the same species indicates clinical infection.

In another embodiment, the rate of change in temperature (not the absolute value per se) of an anatomical structure of an animal relative to the rate of change in temperature of the same anatomical structure in the animal preinfection indicates infection. In another embodiment, the rate of change in temperature (not the absolute value per se) of an anatomical structure of an animal relative to the rate of change in temperature of the same anatomical structure of one or more uninfected animals of the same species indicates infection. In another embodiment, infection of an anatomical structure of an animal is detected if the mean of the temperature information obtained from the infrared thermographic image is preferably greater than 0.2° C., more preferably greater than 0.1° C. the mean of the temperature information for previously obtained infrared thermographic images of the same anatomical structure of the same animal preinfection. In yet another embodiment, infection of an anatomical structure of an animal is detected if the mean of the temperature information obtained from the infrared thermographic image is preferably greater than 0.2° C., more preferably greater than 0.1° C. the mean temperature obtained from infrared thermographic images for the same anatomical structure of one or more uninfected animals of the same species.

In another embodiment of the present invention, inflammation or infection of an anatomical structure is detected if a measure of temperature information for an infrared thermographic image of an anatomical structure of the animal is equivalent to or greater than the predetermined value for the anatomical structure of the animal. Preferably, the predetermined value represents the mean temperature obtained from infrared thermographic images of the same anatomical structure in members of the same species of an animal when there is inflammation or an infection.

In another embodiment of the present invention, inflammation or infection of an anatomical structure of an animal is detected if the change in temperature obtained by successive infrared images of the same anatomical structure of the same animal is greater than a predetermined rate, preferably greater than a rate of 0.1° C./hour. Preferably, successive infrared images of an anatomical structure of an animal are taken every 10, 30 or 60 minutes.

In a further embodiment of the present invention, inflammation of an anatomical structure of an animal is detected if the total temperature of a section of an infrared thermographic image corresponding to one anatomical structure of the animal differs by more than a predetermined amount, preferably 10%, from the total temperature of a section of the infrared thermographic image corresponding to the symmetrical anatomical structure of the animal. The total temperature preferably represents the area or volume of the relevant image section, which can be represented as a number of pixels, multiplied by the mean pixel temperature.

In an embodiment of the present invention, area or volume information alone, independent from temperature information, can be used to detect inflammation of an anatomical structure of an animal. Inflammation of an anatomical structure of an animal is detected if the area or volume of a section of an infrared thermographic image corresponding to one anatomical structure of the animal differs by more than a predetermined amount, preferably 10%, from the area or volume of a section of the infrared thermographic image corresponding to the symmetrical anatomical structure of the animal.

The infrared thermographic temperature information can be normalized or standardized by compensating the temperature information to account for one or more of the following: (i) the state of lactation of the animal; (ii) the state of parity of the animal; (iii) the circadian temperature variation; (iv) the diurnal temperature variation; (v) the animal breed; (vi) the animal housing conditions; or (vii) the geographic location. An adjustment for the state of lactation of an animal would be useful for normalization because animals in early lactation typically have a higher milk production and hence larger udders. An adjustment for the state of parity of an animal would also be useful for normalization because cows, for example, typically in their third or fourth parity will have larger udders than cows in their first parity. Adjustments to normalize the infrared thermographic data depending on when an animal is observed during the day should be performed because an animal's normal temperature will fluctuate over a 24 hour period. The temperature change during the day will also vary with the time of day a cow is milked, hence, a normalization scale would be useful. Adjustments to normalize infrared thermographic data obtained from different breeds of animals should be performed because of differences in their anatomical structures. Furthermore, adjustments to normalize the infrared thermographic data obtained from animals housed differently (e.g., in barns with concrete floors versus in barns with rubber matts) and in different geographic locations (e.g., Edmonton versus Orlando) should be performed.

5.6. Inflammatory Disorders and Infectious Diseases

In one embodiment, inflammatory diseases in an animal, preferably a mammal and most preferably a human are detected using infrared thermography. Examples of inflammatory diseases include, but are not limited to, systemic lupus erythematosus, rheumatoid arthritis, acute respiratory distress syndrome, asthma, osteoporosis, Crohn's disease, reactive arthritis, Lyme disease, multiple sclerosis, contact dermatitis, psoriasis, graft rejection, graft versus host disease, and sarcoidosis. In another embodiment, diseases or disorders that induce an inflammatory response in an animal are detected by infrared thermography. Examples of such diseases and disorders include, but are not limited to, allergic rhinitis, gastrointestinal allergies, food allergies, eosinophilia, conjunctivitis, and glomerular nephritis.

In another embodiment, infectious diseases in an animal, preferably a mammal and most preferably a human are detected using infrared thermography. Infectious diseases include diseases associated with yeast, fungal, viral and bacterial infections. Viruses causing viral infections include, but are limited to, BVD virus, herpes simplex virus (HSV), hepatitis B virus (HBV), hepatitis C virus (HCV), human T-cell lymphotrophic virus (HTLV) type 1 and II, human immunodeficiency virus (HIV), cytomegalovirus, papilloma virus, polyoma viruses, adenoviruses, Epstein-Barr virus, poxviruses, influenza virus, measles virus, rabies virus, Sendai virus, poliomyelitis virus, coxsackieviruses, rhinoviruses, reoviruses, and rubella virus. Bacterial pathogens causing infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (Vibrio) *fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori.*

6. EXAMPLE

Detection of Mastitis Using Infrared Thermography

In order that the invention described herein may be more fully understood, the following examples are set forth. It should be understood that these examples are for illustrative purposes only and are not to be construed as limiting this invention in any manner.

Material & Methods

Twenty mature lactating Holstein cows at 120 days postpartum were housed at the Agriculture and Agri-Food Canada Dairy Research Unit at Lennoxville, Quebec, and were managed in a manner consistent with and representative of the dairy industry in North America, and in compliance with the Canadian Council of Animal Care Guidelines. The left distal quarter of the udder of each animal was infused with 10 μg of E. coli endotoxin (serotype 055:B5, Sigma-Aldrich Co.) in 10 ml of sterile saline.

Fifteen of the cows were additionally treated with experimental inflammation inhibitors. The twenty cows were divided into four treatment groups of five animals each as follows: (i) control, no prophylactic treatment; (ii) aminoguanidine introduced into the cistern of the infected teat; (iii) arginine methyl ester introduced into the cistern of the infected teat; and (iv) dexamethasone introduced into the cistern of the infected teat. The treatments were applied in an effort to attenuate the mastitis response.

Milk samples from the control (right distal) and induced (left distal) quarters of each animal were collected at 13 hours and 1 hour pre-induction and also at 2, 6, 9, 12, 24, 36, 48, 60 and 72 hours post-induction. The milk samples were analyzed for objective indicators of mastitis by conventional analytical procedures as discussed hereinafter. Infrared thermographic images of both distal quarters were simultaneously taken at these times and at 0.5, 1, 1.5, 2 and 2.5 hours post-induction. An Inframetrics 760™ broadband camera (Inframetrics Inc., North Billerica, Mass.) fitted with a 0.5×lens was used to collect the infrared images. Working indoors, images of the posterior surface of the udder of each animal were obtained from a distance of 2.1 m. The Images were recorded on videotape with a videocassette recorder. The analog Images were captured and digitized using a computer equipped with a Matrox Meteor™ video card (Matrox Electronic Systems Ltd., Montreal, Quebec, Canada). The images were saved as bitmap files using Corel Draw™ (Corel Corporation, Ontario, Canada). The bitmap images were calibrated and the udder manually traced to identify the left and right halves of the udder. The image area in number of pixels, and the minimum, maximum and average temperatures, and the standard deviation of the average temperature were recorded and tabulated. Analysis of the data was performed using the computer programs Excel™ (Microsoft Corp., Redmond, Wash., USA) and SAS™ (SAS Institute Inc., Cary, N.C., USA).

The progression of mastitis development was objectively monitored using conventionally known tests such as the somatic cell count in the milk samples (Batra, T. R. and McAllister, A. J., 1984, J. Anim. Sci. 64: 305-312), BSA (Fernando, R. S. et al., 1985, J. Dairy Sci. 449-456), body temperature (Maatje, K. and Rossing, W., 1991, Mastitis Newsletter 16: 6-7), and presence of the enzyme N-acetyl-beta-D-glucosaminidase (NAGase) in the milk samples. NAGase is a lysosomal enzyme secreted in the mammary gland during inflammation. The presence of NAGase in milk is an indication of tissue damage (Perdigon, G. et al., 1986, J. Dairy Sci. 69: 27-31; Fang, W. et al., 1995, J. Dairy Sci. 79: 76-82; Losnedahl, K. J. et al., 1996, Illinois Dairy Report 1-4; Fang, W. and Pyorala, S., 1996, J. Dairy Sci. 79:76-82). By simultaneously testing standard indicators of mastitis and obtaining infrared thermographic images, it was possible to monitor the precise change in infrared characteristics parallel to the standard test results.

Results

Figure 4:
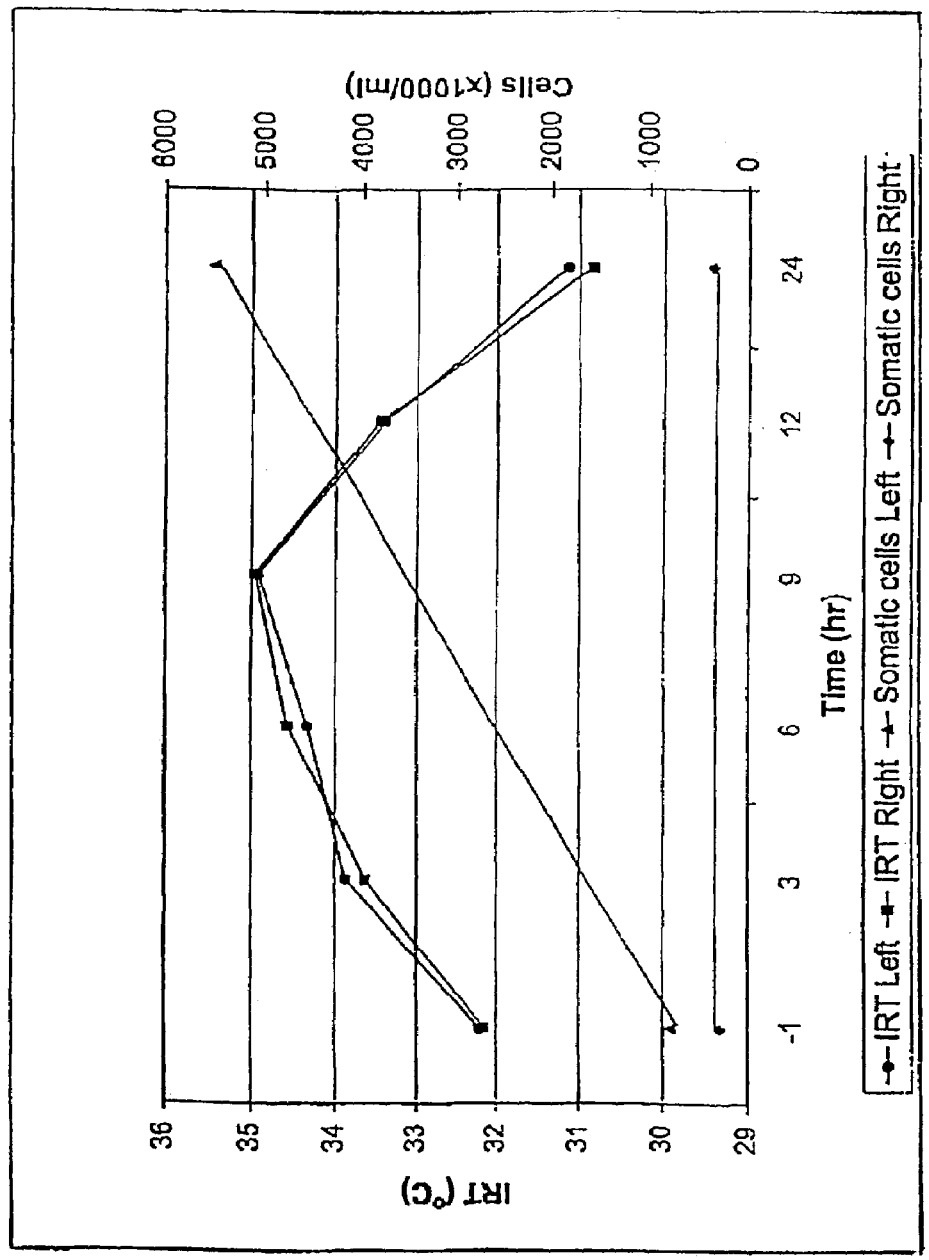
FIG. 4 is a graph of somatic cell count and udder infrared thermography values for milking dairy cows having mastitis induced in the left distal quadrant (n=20). Data for both the left and right distal quarters of the udder are shown.
Figure 5:
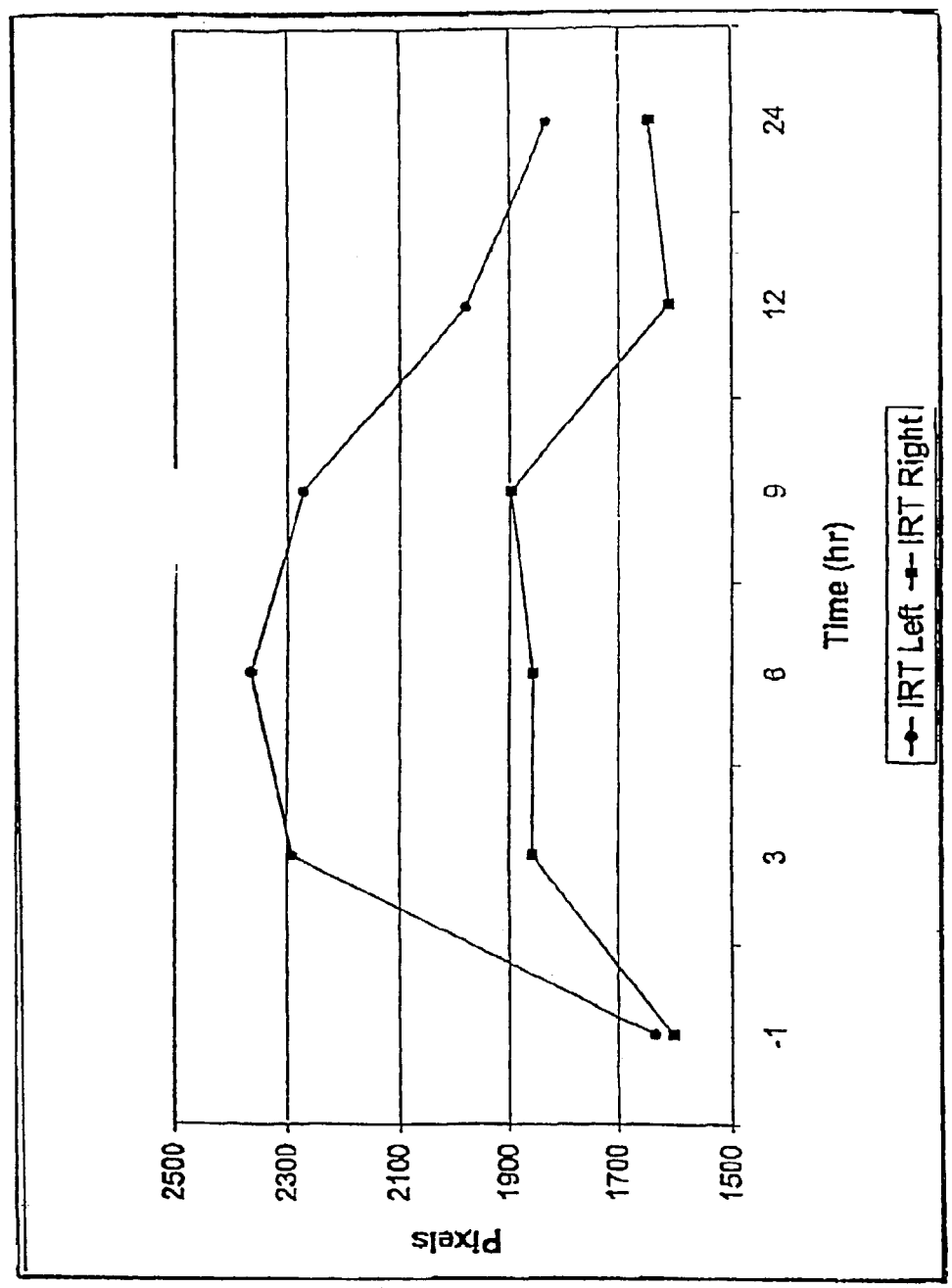
FIG. 5 is a graph of image area (pixels) for the left and right distal quarters of the udder in milking dairy cows having mastitis induced in the left distal quadrant (n=20).
Figure 6:
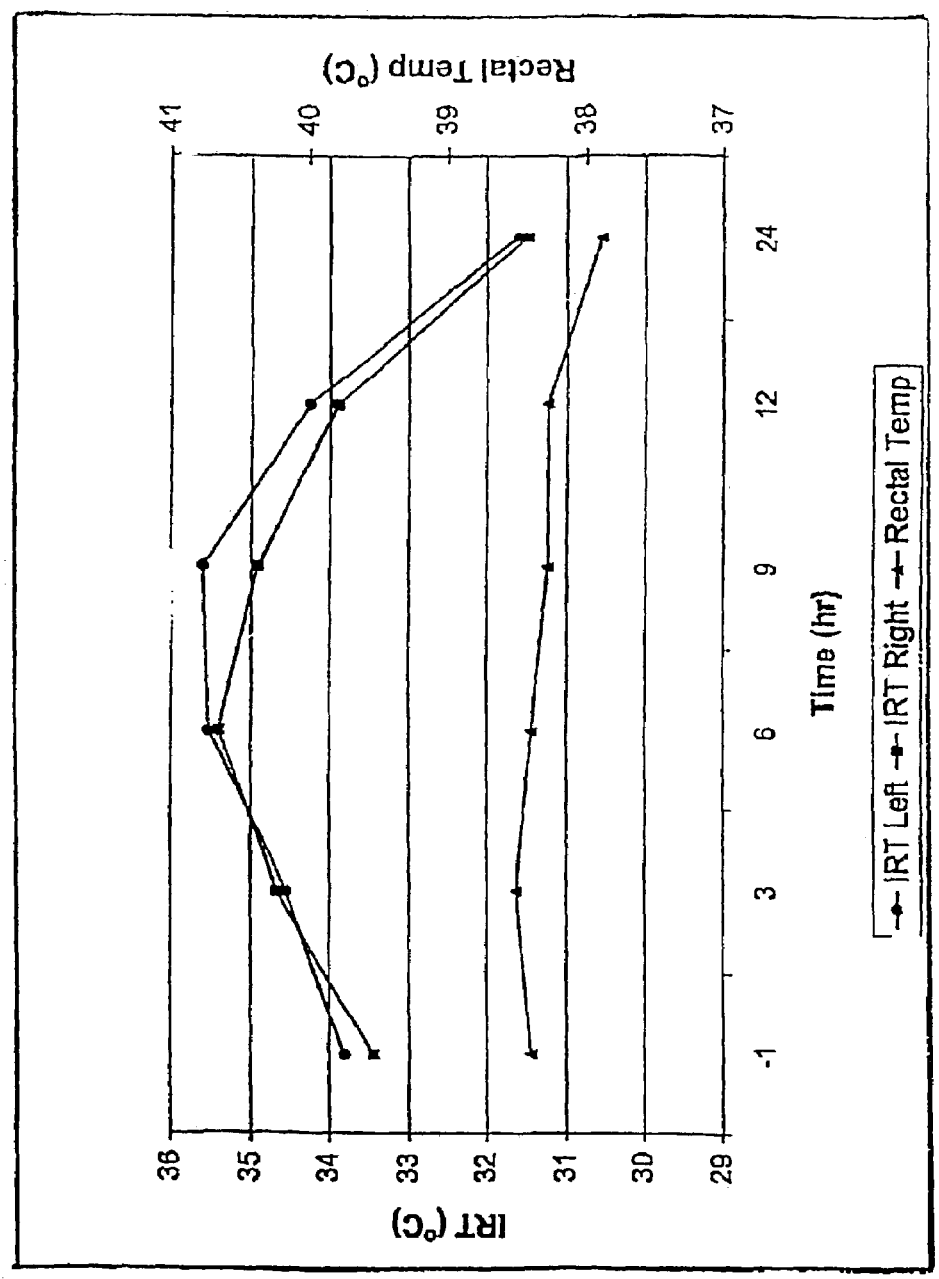
FIG. 6 is a graph is of rectal temperature and udder infrared thermography values for a milking dairy cow (n=1) having mastitis induced in the left distal quarter. Data for both the left and right distal quarters of the udder are shown.
Figure 7:
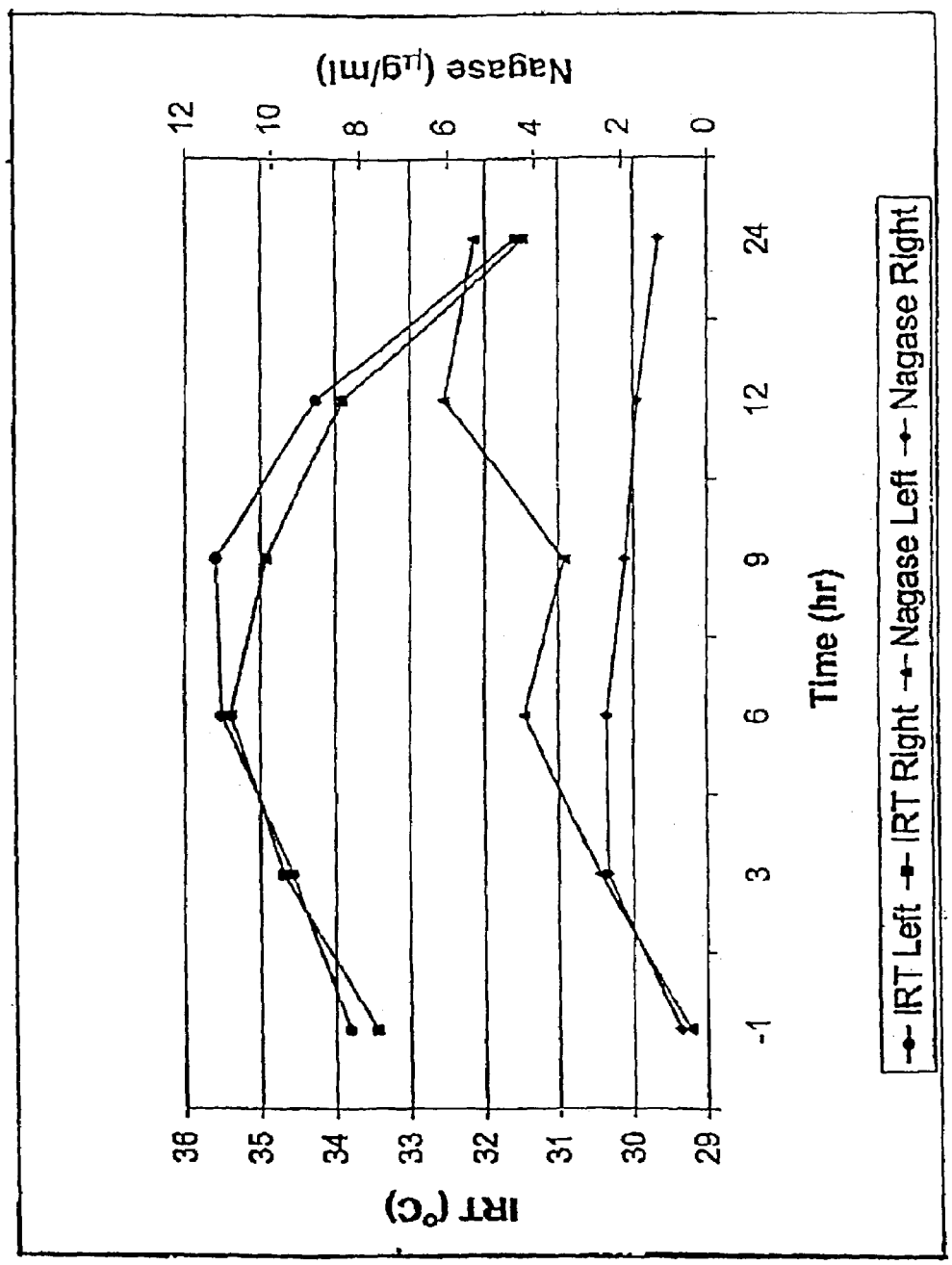
FIG. 7 is a graph of NAGase and udder infrared thermography values for the animal of FIG. 6. Data for both the left and right distal quarters of the udder are shown.
Figure 8:
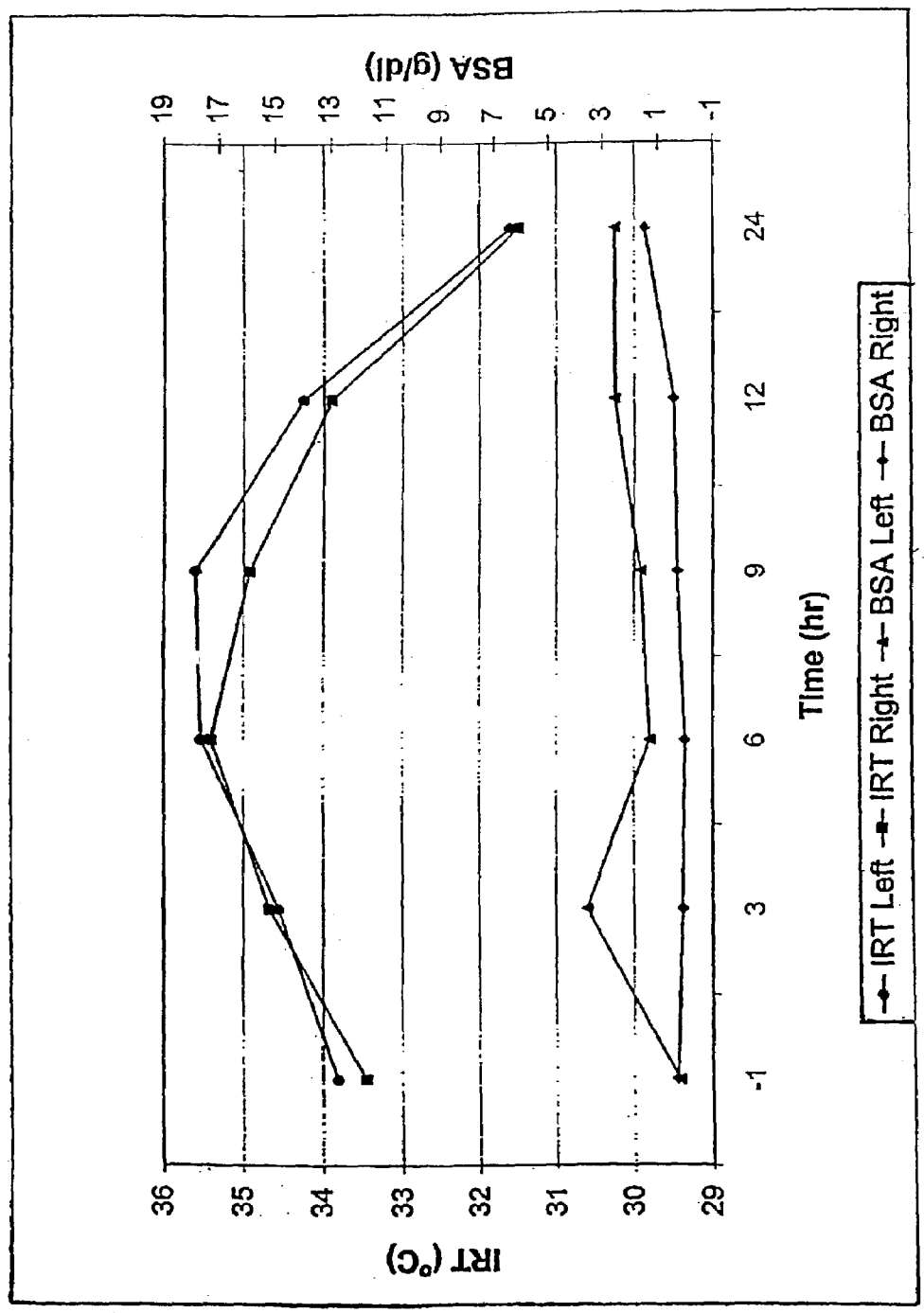
FIG. 8 is a graph of BSA and udder infrared thermography values for the animal of FIGS. 6 and 7. Data for both the left and right distal quarters of the udder are shown.
Figure 9:
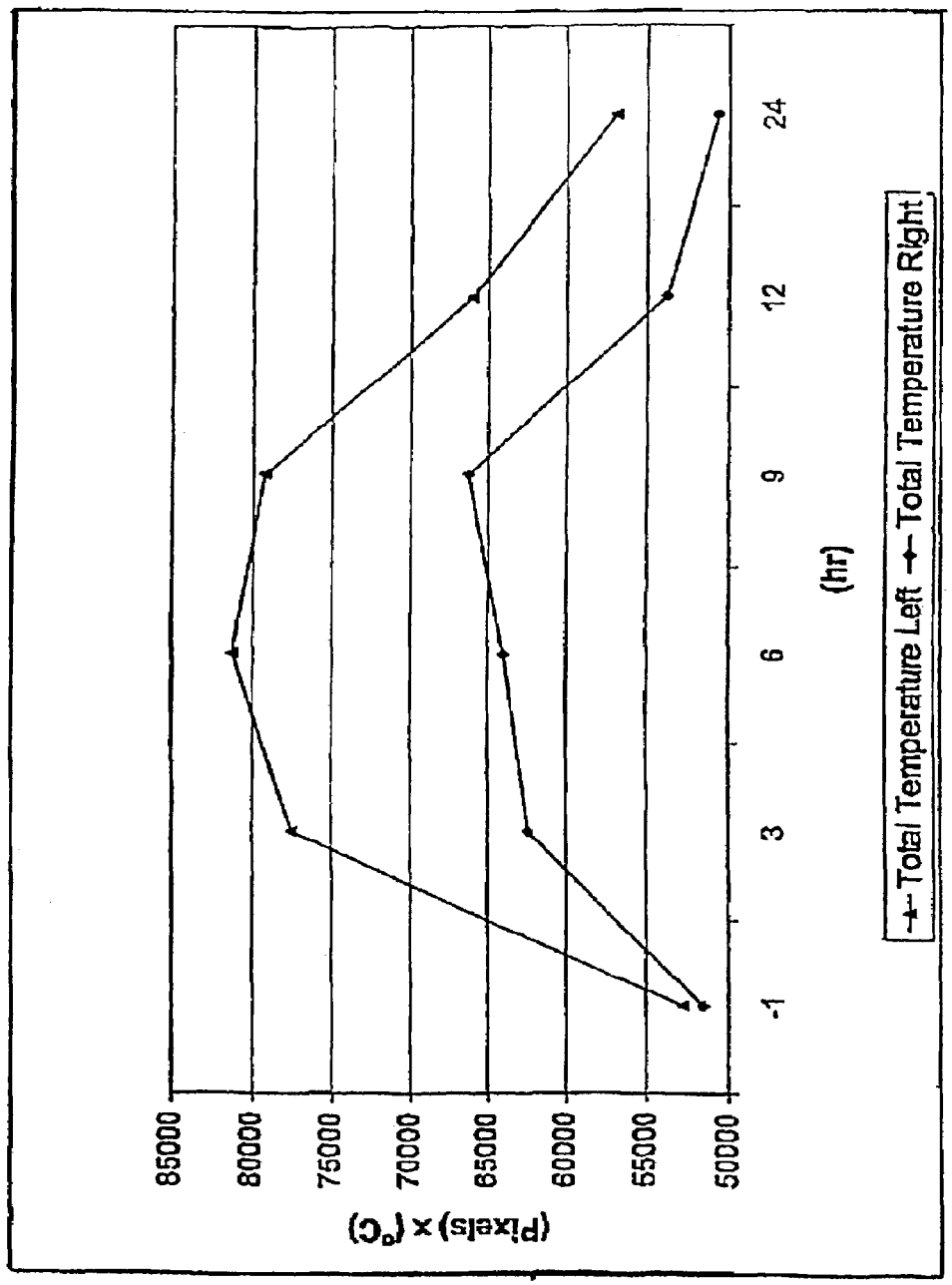
FIG. 9 is a graph of total temperature values (mean udder temperature×image area) for milking dairy cows having mastitis induced in the left distal quadrant (n=20). Data for both the left and right distal quarters of the udder are shown.

The results are presented in tabular form in Tables 1 and 2, and in graphical form in FIGS. 1-9. The treatments with experimental inflammation inhibitors were largely ineffective, and did not significantly change the mastitis response. Therefore, the data in Tables 1 and 2, and FIGS. 1-9, is not presented separately for each of the anti-inflammation treatment groups. FIGS. 6-9 provide least square means of data for the 20 animals tested. FIGS. 6-8 show separately the results obtained from one of the 20 animals tested, the individual animal (reference no. 5029) showing a false-negative result for mastitis when measured by rectal temperature rather than by infrared thermography. The same infrared thermographic ("IRT") data is depicted in each of FIGS. 1-4, plotted along with data obtained from various known techniques for detecting mastitis. FIG. 9 provides the IRT data presented in the form of total temperature (mean temperature×image area or volume).

The results are most readily understood with reference to the figures. FIG. 1 shows the mean temperature of the infrared thermographic image of the left distal quarter of the udder (induced) and the mean temperature of the infrared thermographic image of the right distal quarter of the udder (control) plotted over a 24 hour time course, together with rectal temperature plotted over the same time frame. Based upon the results depicted in FIG. 1, the IRT data for the left and right distal quarters of the udder is very similar, although mastitis was induced only in the left distal quarter. One possible explanation for this is that the high heat transfer capacity through the water found in living cells accounts for the even temperature distribution observed between the distal quarters of the udder. The results from FIG. 1 also indicate that the absolute change in temperature detected by IRT is greater than that detected by measurement of rectal temperature, and that the rate of temperature change detected by IRT is greater than that detected by measurement of rectal temperature. The results in Table 1 indicate that the infrared thermographic image of the udder detected a statistically significant temperature difference ($p<0.05$) by the 1 hour point after mastitis induction, whereas a significant difference in rectal temperature was not detected until much later (the 6 hour point after mastitis induction).

Figure 2:
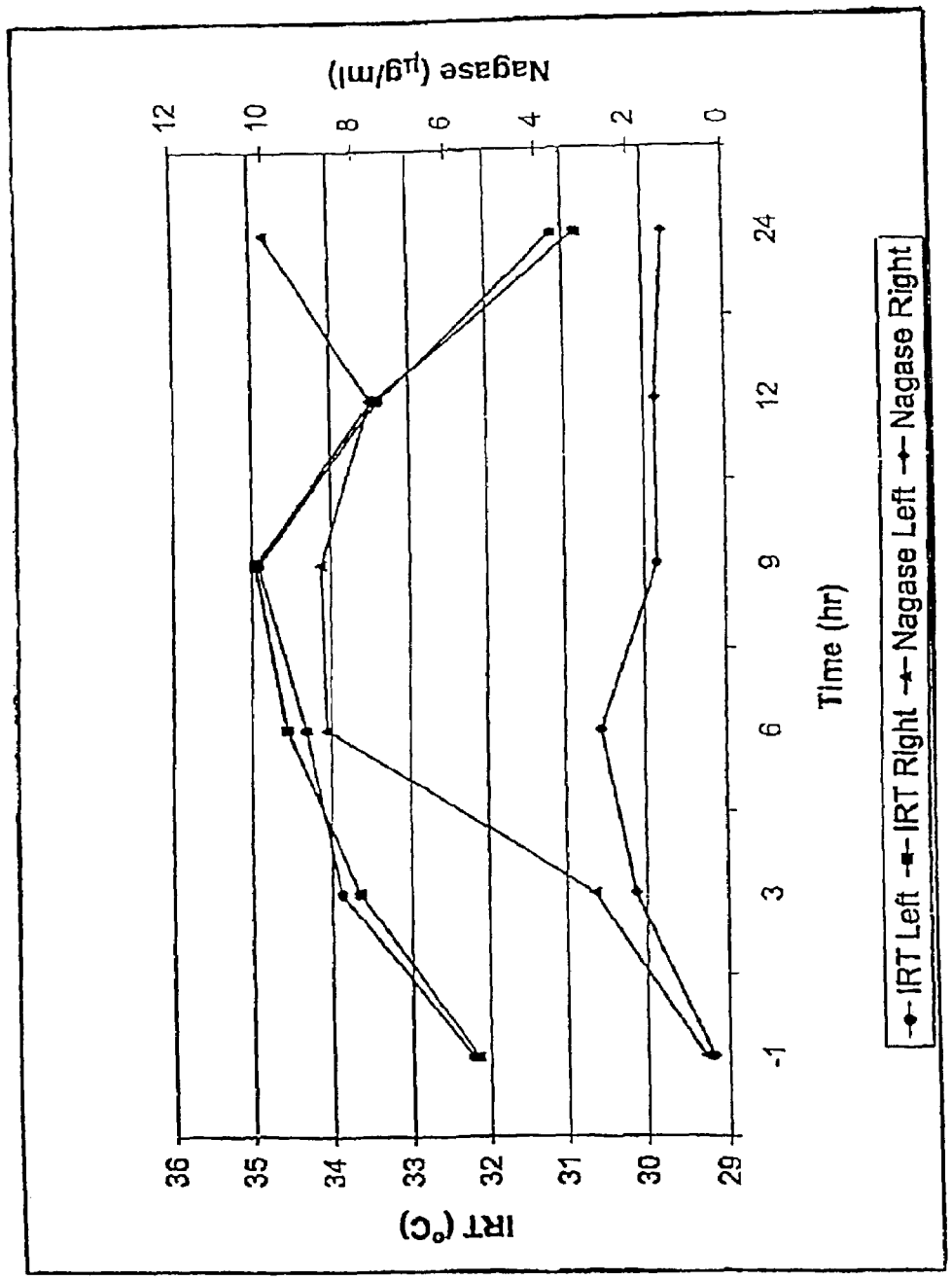
FIG. 2 is a graph of Nagase (N-acetyl-beta-D-glucosaminidase) and udder infrared thermography values for milking dairy cows having mastitis induced in the left distal quadrant (n=20). Data for both the left and right distal quarters of the udder are shown.
Figure 3:
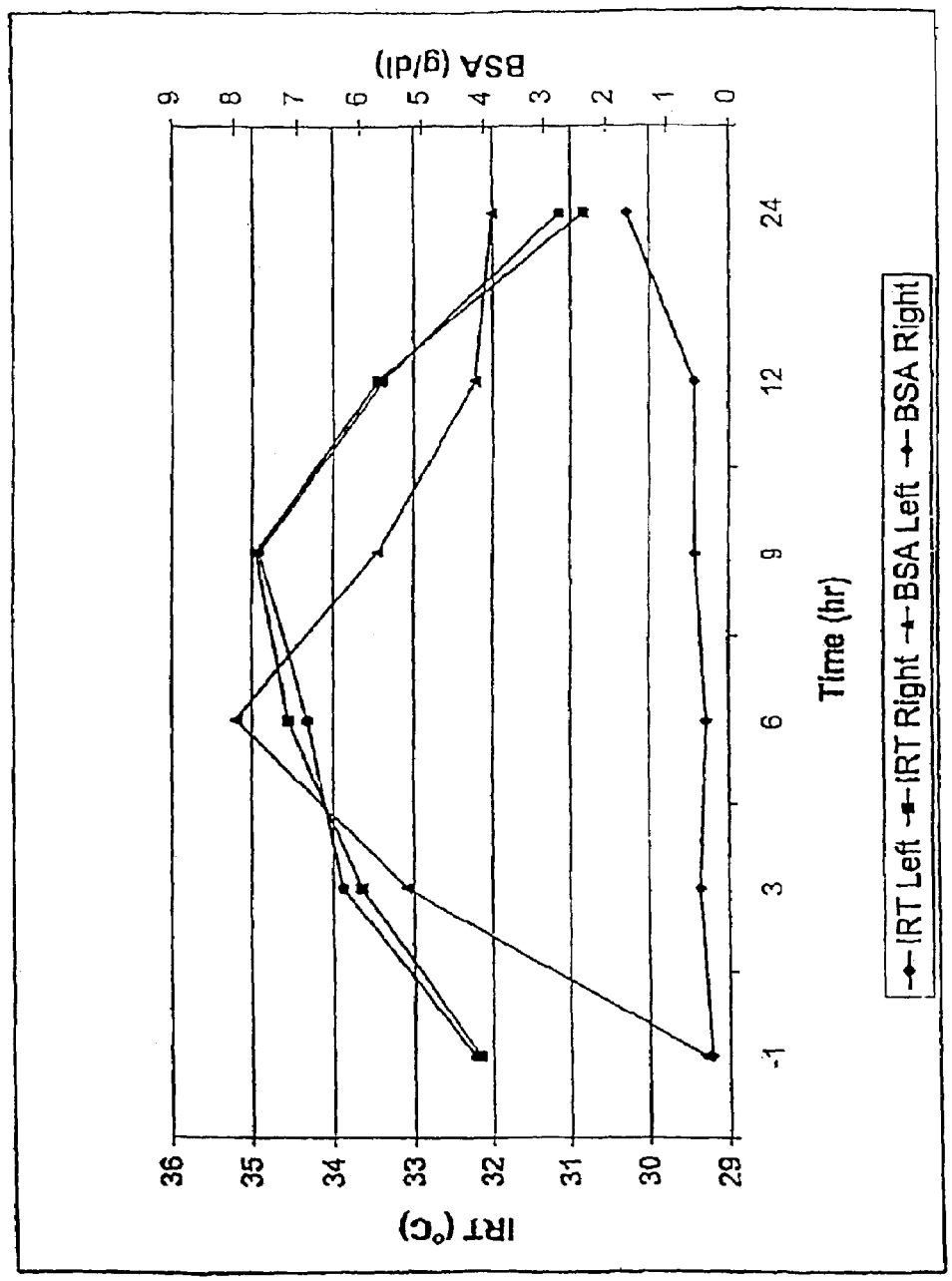
FIG. 3 is a graph of BSA (Bovine Serum Albumin) and udder infrared thermography values for milking dairy cows having mastitis induced in the left distal quadrant (n=20). Data for both the left and right distal quarters of the udder are shown.

FIGS. 2, 3 and 4 plot the same IRT temperature information as in FIG. 1, together with various standard measurements used in the detection of mastitis. FIG. 2 shows the NAGase levels in the left and right distal udder quarters over the first 24 hours after induction of mastitis in the left distal quarter. As expected, the NAGase level in the left distal quarter increased sharply, indicative of mastitis, while there was little change in the NAGase level in the right distal quarter. As discussed earlier, given the separate vascular supplies of the quarters of the udder in cattle, an increase in NAGase level in the non-induced quarter would not be expected. FIGS. 8 and 9 depict similar results, showing, respectively, a significant increase in BSA level and somatic cell count in the left distal udder quarter and little or no change in the right distal quarter. FIGS. 7, 8 and 9 indicate that the mastitis induction model was indeed successful in inducing mastitis in the treated udder quarter, detectable by objective identifiers of mastitis, and that mastitis was also detected by IRT.

FIGS. 6, 7 and 8 emphasize the superior results that can be achieved by the methods of the invention over other temperature measurement techniques. These figures provide data for one of the test animals (animal no. 5029), in which rectal temperature remained nearly unchanged over the first 24 hours after induction of mastitis, whereas mean udder temperature as measured by IRT, changed significantly (FIG. 6). Hence, in an animal in which measurement of rectal temperature disclosed a false-negative result, IRT of the udder correctly detected induced mastitis. Confirmation of induction of mastitis in animal no 5029 is documented in FIGS. 12 and 13 which show, respectively, significantly increased NAGase and BSA levels in the left distal quarter (induced) relative to the right distal quarter (non-induced).

FIG. 5 shows the change in udder quarter area, as represented by number of pixels in an IRT image, for left (induced) and right (non-induced) distal udder quarters for 20 animals over the 24 hour period after mastitis induction. The data in FIG. 5 is independent of temperature, and only refers to the number of pixels in a defined area of the image. It is apparent in FIG. 5 that the swelling of the left distal quarter of the udder relative to the right distal quarter (resulting in a lack of symmetry) as a result of mastitis induction was readily detected from the IRT image.

FIG. 9 combines IRT image area and mean image temperature as a total temperature (mean pixel temperature× number of pixels). In FIG. 1, there was a very close symmetry between the IRT temperature of the left distal quarter and that of the right distal quarter, presumably due to the high heat transfer capacity of living cells. Conversely, in FIG. 9, the left distal quarter (induced) exhibits a much higher total temperature than the right distal quarter (non-induced). The temperature information remains the same as in FIG. 1, but the greater area of the portion of the image representative of the left distal quarter of the udder relative to the area of the right distal quarter (as a result of swelling in response to mastitis) is reflected in the total temperature measurement.

Referring again to FIG. 1 and to Table 1, it will be appreciated that the mean IRT image temperature at the time −1 h (1 hour before induction of mastitis) reflects the IRT image temperature of the udder when the animals do not have mastitis, and therefore acts as a control IRT temperature for the animals in a healthy state. In the period from 3 hours post-induction and 12 hours post-induction, the mean IRT temperature for both the left and right hind udder quarters for the 20 animals was less than 1° C. greater than the control value of 32.19° C. Hence, an IRT udder temperature less than 1° C. greater than a control value for an animal in a healthy state is indicative of mastitis in a subject mammal.

FIG. 1 and Table 1 shows that, during the first 24 hours after induction of the mastitis model, mean IRT temperature for both the left and right distal udder quarters for the 20 animals tested changed at a rate of at least 0.1° C. per hour, whether increasing or decreasing. Hence, a rate of change of IRT temperature of at least 0.1° C. per hour is indicative of mastitis in a subject mammal.

FIG. 5 shows that during the first 24 hours after induction of mastitis in the left distal quarter of the udder, the area of the portion of the image corresponding to the induced quarter is at least 10% greater than that of the non-induced (control) right distal quarter of the udder. Thus, if the area of a portion of the image corresponding to a first quarter of the udder of the animal differs from the area of a portion of the image corresponding to a second quarter of the udder of the animal by greater than 10%, this is indicative of mastitis in the animal.

Similarly, referring to FIG. 9 and Table 2, during the first 24 hours after induction of mastitis in the left distal quarter of the udder, the total temperature (mean pixel temperature× number of pixels) of the portion of the image corresponding to the induced quarter is at least 10% greater than that of the non-induced (control) right distal quarter of the udder. Thus, if the total temperature of a portion of the image corresponding to a first quarter of the udder of the animal differs from the total temperature of a portion of the image corresponding to a second quarter of the udder of the animal by greater than 10%, this is indicative of mastitis in the animal.

7. EXAMPLE

Detection of Infection Using Infrared Thermography

Fifteen British cross heifers seronegative for BVD and IBR were weaned from the main herd following standard Animal Disease Research Institute (ADRI; Lethbridge, Alberta) protocol and allocated to one of two treatment groups balanced by weight, body condition, age, coat color and hair condition. The two treatment groups consisted of: (1) five control, uninfected animals; and (2) ten BVD virus infected animals. The calves were housed in groups of five in three separate environmentally controlled rooms and the body weights of the calves were collected before the study began and after the study ended.

All of the calves were given a balanced alfalfa and barley ration which was designed to 1.5 times maintenance based on NRC recommendations, and all calves were given ad libitum access to fresh water. Further, a rubberized mat bedding was provided for the animals to lay upon. The three animal rooms used in the study were all kept at a constant temperature and humidity (approximately 24° C. and 28% humidity) with barometric pressure held constant. Lighting was adjusted to simulate normal daylight and darkness (12 hours of light and 12 hours of dark). The calves were weaned and placed into their isolation rooms for a period of 14 days prior to infection with BVD virus to allow the animals to acclimatize to the rooms, people and procedures.

A hand held portable Inframetrics broadband 760 camera was used to collect infrared thermographic images. Infrared thermographic images were captured for all of the animals at a fixed time every day. Lateral eye images consisting of the eye orbital socket plus approximately 1 cm around the socket were captured daily. Frontal nose infrared thermographic images consisting of approximately 3 $cm^2$ located immediately between and above the nostrils were obtained daily. Frontal ear infrared thermographic consisting of an area approximately 2 $cm^2$ in the middle of the inner ear surface were obtained daily. Left side (lateral) infrared thermographic images representing about 20% of the animal's total surface area were obtained. While this lateral image does not contain many thermoregulatory sites the side is nonetheless, like the dorsal image, representative of an average surface infrared temperature. Dorsal infrared thermographic images consisting of a square area representing approximately 35000 pixels or probably 15% of the animals surface area were also obtained daily.

Animals were not captured when imaged but instead a technician walked around the animals to obtain the infrared thermographic images. Further, two separate Inframetrics cameras were used to obtain the infrared thermographic images of the control animals and the BVD virus infected animals.

In addition to the infrared measurements taken, clinical and physiological measurements were taken on days 0, 3, 6, 9 and 12 postinfection. The calves were captured in a head gate and 10 ml of blood was collected in a vacutainer by venus puncture. From this blood sample, measurements of differential blood cell counts, cortisol, IgA and basic hematology (CBC) were performed. Also, viral titer and serological assays were performed. Further, health clinical scores were monitored on all of the calves daily using the score system developed by ADRI (Table 3).

All of the animals were humanely euthanized toward the end of the disease course. Necropsy was performed on all animals using established scoring procedures.

Results

Infrared Thermographic Images of the Eye of Calves

As evident from the results in Table 4, eye infrared temperatures in animals infected with BVD virus increased throughout the BVD disease course relative to the eye infrared temperatures for the same animals preinfection. Statistically significant increases in the eye temperature (0.9° C., $p<0.01$) were observed as early as one day postinfection and a maximum separation of 2.6° C. from controls was obtained. In contrast to the early changes detected using infrared thermography, the presence of virus specific antibody was not detectable until 5 or 6 days postinfection and statistically significant changes in clinical scores were not evident until eight days postinfection (Table 5). Further, there was no statistically significant evidence of changes in objective measures of disease such as haptoglobin until 10 days postinfection.

In comparison to the control animals, the BVD virus infected calves did not show any consistent signs in eye temperature increase until 4 days postinfection. The eye temperatures for the BVD virus infected animals obtained a maximum separation of over 2° C. by day 10 postinfection. The increases in the mean temperatures of the eye of BVD virus infected animals proved to be statistically significant and were obtained several days before significant differences in clinical scores were observed. Further, when clinical scores were high enough to verify the presence of BVD, a Spearman Ranking test indicated that animals with the highest clinical scores were also the animals with the highest infrared eye temperature ($P<0.05$). Therefore, the eye temperatures obtained using infrared thermography indicate that infrared thermography can be used to detect infection several days to one week prior to detection using conventional subjective (clinical scores; Table 5) or objective measurements such as haptoglobin (Table 6).

Infrared Thermographic Images of the Nose of Calves

As evident from the results in Table 7, the nose infrared temperatures for the BVD virus infected calves began to elevate significantly as early as 4 days postinfection. Compared to their control, preinfection temperatures, the BVD virus infected animals displayed a change in temperature (i.e., delta T value) of just under 4° C. by 9 to 10 days postinfection. The BVD virus infected animals displayed a delta T value of 4.6° C. compared to uninfected control animals. Similar to the eye temperatures, the delta T values obtained for the nose were statistically significant compared to either the animals own initial preinfection temperature or to control animals on comparative days. Thus, the nose temperatures measured using infrared thermography in the BVD virus infected animals demonstrate that temperature changes detected by infrared thermography parallel the changes seen in the course of an infectious disease. Further, these results demonstrate that infrared thermography can be used to detect infection several days earlier than clinical scores (Table 5) or objective biological measurements for infection such as haptoglobin (Table 6).

Infrared Thermographic Images of the Ear of Calves

As evident from the results in Table 8, ear temperatures for the BVD infected animals started to increase as early as 1 to 2 days postinfection and a maximum delta T value of approximately 4° C. for mean temperatures 10 days postinfection. This was one of the largest delta T values obtained for any of the anatomical structures measured. However, consistent with the fact that ears are known to be involved in more acute thermoregulation in a homeothermic animal, the ear temperatures obtained were highly variable. The variation in the ear temperatures obtained was the greatest in the BVD virus infected animals. Despite the large, statistically significant delta T values obtained when comparing BVD virus infected animal temperatures to preinfection, baseline temperatures, the delta T values obtained when comparing BVD virus infected animal temperatures to control, uninfected animal temperatures were not high. Further, unlike eye temperatures, the ranking statistics were not highly significant for ear temperatures.

Thus, ear temperature measurements using infrared thermography in BVD infected animals parallel the course of the disease. Further, ear temperature measurements using infrared thermography are at least as indicative of illness as clinical scores. However, the high degree of variability in ear temperatures suggests that infrared thermographic images of this particular anatomical structure would be less reliable for early detection of an infectious disease.

Infrared Thermographic Images of the Left Side of Calves

The data presented in Table 9 indicates that the lateral temperature changes obtained using lateral infrared thermographic images are not as sensitive or revealing as the eye or nose temperature changes for the detection of infection. Further, the lateral infrared data was somewhat variable compared to the eye or nose infrared data obtained. Nonetheless, as with the eye infrared data, the lateral images demonstrated that compared to their own control temperatures on the day of infection, the BVD virus infected cattle showed a statistically significant increase in infrared temperature as early as one day postinfection. Statistically significant changes in the mean temperature as determined using infrared thermography were detected as much as 5 to 7 days before significant statistical changes in subjective clinical scores (Table 5) or objective biological scores such as haptoglobin (Table 6) were evident.

Statistically significant differences in the mean temperature in BVD virus infected cattle compared to the mean temperature in uninfected control animals was detected at about 8 days postinfection or about the time when the earliest clinical symptoms were beginning to appear. Nonetheless, the lateral infrared data demonstrates that infrared thermography can be used to identify animals with an infectious disease at the very least as early as the earliest clinical scores and in many cases, one to several days before the presence of clinical scores.

Infrared Thermographic Images of the Dorsal Side of Calves

The results in Table 10 illustrate that the BVD virus infected animals begin to show statistically significant increases in dorsal temperatures about 6 to 7 days postinfection and reach a delta T value of 1.8° C. compared to their own initial preinfection temperatures. Compared to uninfected controls, statistically significantly delta T values of about 1.5° C. were obtained in BVD virus infected animals. Further, as with the other infrared thermographic images, increases in dorsal temperatures observed in infected animals coincided with or preceded by several days the changes detected in clinical scores (Table 5) and objective biological assays such as haptoglobin (Table 6).

TABLE 1

Time course for infrared temperature measured by infrared thermography, rectal temperature and milk analysis parameters in cows utilized in a mastitis induction model (n = 20). Data represent least squares means.

| Time (h) | Rectal Temp °F. | Infrared Temp °C. | NAGase µg/ml | Somatic Cell Counts | BSA g/dl |
|---|---|---|---|---|---|
| −1 | 101.2a | 32.19a | 0.39a | 504a | 0.329a |
| 0.5 | 101.3a | 32.36ab | | | |
| 1 | 102.0a | 32.77bc | | | |
| 2 | 102.0a | 32.97cd | | | |
| 3 | 102.7a | 33.76e | 2.39b | | 2.86b |
| 6 | 105.3b | 34.44f | 5.66b | | 4.17b |
| 9 | 102.2a | 34.94d | 5.15b | | 3.13b |
| 12 | 96.7b | 33.42d | 4.58b | | 2.35b |
| 24 | 100.9a | 30.99 | 5.64b | 2875b | 2.76b |
| 36 | 101.2 | 33.15 | 5.59b | 2753b | 1.50b |
| 48 | 101.1 | 31.43 | 4.72b | 1849b | 0.87a |
| 60 | 101.7 | 33.11 | 3.46b | 1370b | 1.03a |
| 72 | 101.1 | 31.68 | 2.44a | 933a | 0.67a | a,b,—means with different letters within columns are significantly different ($P < 0.05$)

TABLE 2

Time course for mean total temperature values (infrared thermographic temperatures X udder area in pixels) for left, distal udder quarter (mastitis induced) and right, distal udder quarter (non-induced) in lactating dairy cows. Values represent least squares means for 20 cows.

| Time (h) | Total Temperature Values for Left (induced) and Right (non-induced; control) Udders | | |
|---|---|---|---|
| | Left | Right | |
| −1 | 52755 a | 51486 a | X |
| 3 | 77553 b P = 0.001 | 62395 b P = 0.002 | Y |
| 6 | 81294 b P = 0.001 | 63998 b P = 0.001 | Y |
| 9 | 79250 b P = 0.001 | 66237 b P = 0.001 | Y |
| 12 | 66017 b P = 0.002 | 53782 a P = 0.50 | Y |
| 24 | 56916 a P = 0.23 | 50630 a P = 0.81 | Y |
| 36 | 60989 b P = 0.02 | 54157 a P = 0.44 | Y |
| 48 | 59322 b P = 0.06 | 54015 a P = 0.47 | X |
| 60 | 61971 b P = 0.008 | 55370 a P = 0.26 | X |
| 72 | 56745 a P = 0.25 | 55571 a P = 0.24 | X | a,b,—means with different letters within columns are significantly different ($P < 0.05$)
X,Y,—means with different letters within rows are significantly different ($P < 0.05$). Left is the mastitis induced distal quarter, right is the distal, non-induced quarter (control).

TABLE 3

Clinical Scores

| Clinical Sign | Score |
|---|---|
| Lethargy | 0 = none |
| | 1 = mild anorexia or listlessness |
| | 2 = moderate lethargy, slow to rise, anorectic |
| | 3 = recumbent |
| | 4 = death |
| Hemmorhage | 0 = none |
| | 1 = few petechiae on smucous membranes or sclera |
| | 2 = moderate or severe petechiation or heatomas >1 |
| | 3 = large hematomas >5 cm |
| | 4 = bloody diarrhea or epstaxis |
| Respiratory Signs | 0 = none |
| | 1 = clear nasal discharge or slight cough, no treatment required |
| | 2 = mucopurulent discharge or severe cough, slight increase in lung sounds |
| | 3 = severe pneumonia |

TABLE 3-continued

Clinical Scores

| Clinical Sign | Score |
|---|---|
| Diarrhea | 0 = none |
| | 1 = mild or slight, <5% dehydrated |
| | 2 = moderate, 5 to 10% dehydrated |
| | 3 = severe or profuse, >10% dehydrated |

TABLE 4

Eye Infrared Thermographic Values

| Day | Mean Temperature in BVD Virus Infected Calves | Mean Temperature in Control Calves |
|---|---|---|
| 0 | 31.22 ax | 32.0 y |
| 1 | 32.11 bx | 30.54 y |
| 2 | 32.26 b | 33.62 y |
| 3 | 32.40 b | 32.64 y |
| 4 | 32.54 bx | 31.90 (0.3) |
| 5 | 32.66 bx | 31.54 y |
| 6 | 32.89 bx | 31.82 y |
| 7 | 33.31 bx | 31.33 y |
| 8 | 33.51 bx | 31.47 y |
| 9 | 33.38 bx | 30.57 y |
| 10 | 33.79 bx | 31.64 y | a,b means with different letters within columns are significantly different $P < 0.01$ using 2 tailed paired T-test
x,y means with different letters within rows are significantly different $P < 0.01$ using 2 tailed unpaired T-test

TABLE 5

Summary of Clinical Scores

| Day | Mean Clinical Scores in BVD Virus Infected Calves | Mean Clinical Scores in Control Calves |
|---|---|---|
| 0 | 0 | 0 |
| 1 | 0.1 | 0 |
| 2 | 0.1 | 0 |
| 3 | 0.1 | 0 |
| 4 | 0 | 0 |
| 5 | 0 | 0 |
| 6 | 0.1 | 0 |
| 7 | 0.3 | 0 |
| 8 | 0.9 | 0.2 |
| 9 | 2.2 | 0.1 |
| 10 | 2.9 | 0 |
| 11 | 3.2 | 0 |
| 12 | 2.7 | 0 |
| 13 | 1.2 | 0 |

TABLE 6

Serum Haptoglobin in BVD Infected and Uninfected Calves

| Day | BVD Values (µg/ml) | Control Values (µg/ml) |
|---|---|---|
| 0 | <15 (one animal at 567) | <15 |
| 3 | 308 (increase due to 2 animals) | <15 |
| 7 | 218 (increase due to 2 animals) | <15 |
| 10 | 803 (all animals increase) | <15 |

TABLE 7

Nose Infrared Thermographic Values

| Day | Mean Temperature in BVD Virus Infected Calves | Mean Temperature in Control Calves |
|---|---|---|
| 0 | 29.1 a | 28.51 |
| 1 | 29.61 ax | 26.89 y |
| 2 | 29.43 a | 29.88 |
| 3 | 29.96 a | 28.68 |
| 4 | 31.52 bx | 29.9 y.06 |
| 5 | 31.03 bx | 28.7 y.05 |
| 6 | 31.48 bx | 28.7 |
| 7 | 32.48 bx | 29.46 y |
| 8 | 32.9 bx | 29.74 y |
| 9 | 33.14 bx | 28.58 y |
| 10 | 32.77 bx | 29.48 y | a,b means with different letters within columns are significantly different P < 0.01 using 2 tailed paired T-test
x,y means with different letters within rows are significantly different P < 0.01 using 2 tailed unpaired T-test

TABLE 8

Ear Infrared Thermographic Values

| Day | Mean Temperature in BVD Virus Infected Calves | Mean Temperature in Control Calves |
|---|---|---|
| 0 | 22.38 a | 23.35 |
| 1 | 22.41 a | 22.58 |
| 2 | 23.29 a | 24.76 |
| 3 | 23.19 a | 24.95 |
| 4 | 23.89 b.06 | 24.90 |
| 5 | 24.1 b.09x | 23.13 |
| 6 | 24.6 b.02x | 23.14 y.25 |
| 7 | 25.9 b.01 | 24.56 |
| 8 | 25.4 b.04 | 23.9 |
| 9 | 23.93 a | 22.2 |
| 10 | 26.3 b.04x | 22.7 y.07 | a,b means with different letters within columns are significantly different P < 0.05 using 2 tailed paired T-test
x,y means with different letters within rows are significantly different P < 0.05 using 2 tailed unpaired T-test

TABLE 9

Lateral Infrared Thermographic Values

| Day | Mean Temperature in BVD Virus Infected Calves | Mean Temperature in Control Calves |
|---|---|---|
| 0 | 21.87 ax | 213.2 y.05 |
| 1 | 22.61 b | 22.2 |
| 2 | 22.6 b.07x | 23.95 y |
| 3 | 22.55 a.1 | 22.38 y |
| 4 | 22.89 b | 23.16 y |
| 5 | 22.58 b.07 | 22.43 y |
| 6 | 22.71 b | 22.52 y |
| 7 | 23.2b x | 22.07 y.04 |
| 8 | 23.39 bx | 22.0 y.03 |
| 9 | 23.1 b.02x | 21.66 y |
| 10 | 23.84 bx | 22.11 y | a,b means with different letters within columns are significantly different P < 0.01 using 2 tailed paired T-test
x,y means with different letters within rows are significantly different P < 0.01 using 2 tailed unpaired T-test

TABLE 10

Dorsal Infrared Thermographic Values

| Day | Mean Temperature in BVD Virus Infected Calves | Mean Temperature in Control Calves |
|---|---|---|
| 0 | 22.29 ax | 20.62 y |
| 1 | 22.74 ax | 21.26 y |
| 2 | 23.04 b | 23.90 |
| 3 | 22.44 a | 22.48 |
| 4 | 23.08 b | 22.65 |
| 5 | 22.70 a | 22.23 |
| 6 | 22.75 a(0.056) | 22.15 |
| 7 | 22.95 bx | 21.59 y |
| 8 | 23.54 bx | 21.96 y |
| 9 | 23.06 bx | 21.47 y |
| 10 | 24.08 bx | 22.58 y | a,b means with different letters within columns are significantly different P < 0.05 using 2 tailed paired T-test
x,y means with different letters within rows are significantly different P < 0.05 using 2 tailed unpaired T-test The present invention is not to be limited in scope by the specific embodiments described herein, which are intended as single illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All references cited herein are incorporated herein by reference in the entirety for all purposes.

What is claimed is:

1. A method for detecting infection of an animal, comprising the steps of:
   (a) scanning a selected anatomical structure selected from a mammary gland, an eye, a nose or an ear of the animal with an infrared camera to obtain an infrared thermographic image of the selected anatomical structure of the animal;
   (b) processing the image to provide a measure of temperature information selected from a measure of central tendency, a measure of dispersion, or total temperature for only a portion of the image representing the selected anatomical structure;
   (c) comparing the measure of the temperature information to a predetermined value, the predetermined value being a measure of central tendency, a measure of dispersion, or total temperature obtained from only a portion of one or more infrared thermographic images representing the same selected anatomical structure of either the same animal pre-infection or the same selected anatomical structure of a population of uninfected animals of the same species; and
   (d) detecting subclinical, early or clinical infection of the animal if the measure of the temperature information is greater than the predetermined value by at least a predetermined amount.

2. The method according to claim 1, wherein the animal is a mammal.

3. The method according to claim 1, wherein an infection is detected if the measure of the temperature information is a change in the mean temperature greater than 0.5° C. of the selected anatomical structure relative to the mean temperature of the same anatomical structure of the same animal preinfection.

4. The method according to claim 3, which comprises detecting early or subclinical infection of the animal if the measure of the temperature information is a change in the mean temperature of less than 1° C. of the selected anatomical structure relative to the mean temperature of the same anatomical structure of either the same animal preinfection, or a population of uninfected animals of the same species.

5. The method according to claim 1, wherein an infection is detected if the measure of the temperature information is a change in the mean temperature greater than 1° C. of the selected anatomical structure relative to the mean temperature of the same anatomical structure of the same animal preinfection.

6. The method according to claim 1, wherein an infection is detected if the measure of the temperature information is a change in the mean temperature greater than 0.5° C. of the selected anatomical structure relative to the mean temperature of the same anatomical structure in a population of uninfected animals of the same species.

7. The method according to claim 1, wherein an infection is detected if the measure of the temperature information is a change in the mean temperature greater than 1° C. of the selected anatomical structure relative to the mean temperature of the same anatomical structure in a population of uninfected animals of the same species.

8. The method according to claim 1, wherein the infection being detected is mastitis, the animal is a mammal and the selected anatomical structure is a mammary gland.

9. The method according to claim 8, comprising the steps of:
   (a) obtaining one or a plurality of infrared thermographic images of the mammary gland of the mammal, wherein the one or a plurality of infrared thermographic images provide the measure of the temperature information representative of the mammary gland;
   (b) comparing the measure of the temperature information representative of the mammary gland to the predetermined value; and
   (c) detecting the presence of mastitis in the mammal if the measure of the temperature information is greater than the predetermined value by the predetermined amount.

10. The method according to claim 9, wherein the predetermined value is selected from the group consisting of:
   (i) the measure of the temperature information of the mammary gland of the same mammal unaffected by mastitis; and
   (ii) the measure of the temperature information of the mammary gland of a population representative of the mammal, wherein the population comprises mammals unaffected by mastitis.

11. The method according to claim 10, wherein the measure of the temperature information is a measure of central tendency.

12. The method according to claim 11, wherein the measure of central tendency is a mean.

13. The method according to claim 12, wherein the predetermined amount is at least 0.1° C.

14. The method according to claim 12, wherein the predetermined amount is greater than 0.5° C.

15. The method according to claim 12, wherein the predetermined amount is greater than 1° C.

16. The method according to claim 10, wherein the plurality of images are obtained successively over time to identify the mammal as having mastitis if the change over time of the measure of the temperature information provided by the plurality of images is greater than a predetermined rate.

17. The method according to claim 16, wherein said predetermined rate is 0.1° C. per hour.

18. The method according to claim 10, wherein the mammal is a non-human mammal.

19. The method according to claim 10, wherein the mammal is selected from a cow, pig, horse, dog or cat.

20. The method according to claim 10, wherein the mammal is of the species *Bos taurus* or *Bos indicus*.

21. The method according to claim 20, wherein the mammary gland is an udder.

22. The method according to claim 21, wherein a first image is obtained of one quarter of the udder at time 0 and a second image is obtained of the same quarter of the udder at a later time.

23. The method according to claim 22, wherein a total temperature of the first image and a total temperature of the second image are determined.

24. The method according to claim 23, wherein mastitis is detected if the total temperature of the first image differs from the total temperature of the second image by greater than the predetermined amount.

25. The method according to claim 24, wherein the total temperature of the first image is determined by multiplying the area represented by the first image by the mean of the temperature information provided by the first image, and the total temperature of the second image is determined by multiplying the area represented by the second image by the mean of the temperature information provided by the second image.

26. The method according to claim 25, wherein the predetermined amount is 10%.

27. The method according to claim 24, wherein the mammal is a non-human mammal.

28. The method according to claim 24, wherein the mammal is of the species *Bos taurus* or *Bos indicus*.

29. The method according to claim 21, wherein a first image is obtained of one frontal quarter or one rear quarter of the udder, and a second image is obtained of the other frontal quarter or the other rear quarter of the udder.

30. The method according to claim 29, wherein a total temperature of the first image and a total temperature of the second image are determined.

31. The method according to claim 30, wherein mastitis is detected if the total temperature of the first image differs from the total temperature of the second image by greater than the predetermined amount.

32. The method according to claim 31, wherein the total temperature of the first image is determined by multiplying the area represented by the first image by the mean of the temperature information provided by the first image, and the total temperature of the second image is determined by multiplying the area represented by the second image by the mean of the temperature information provided by the second image.

33. The method according to claim 32, wherein said predetermined amount is 10%.

34. The method according to claim 31, wherein the mammal is a non-human mammal.

35. The method according to claim 31, wherein the mammal is of the species *Bos taurus* or *Bos indicus*.

36. The method according to claim 1, wherein the infection being detected is bovine viral diarrhea and the selected anatomical structure is the eye, the nose or the ear.

37. The method according to claim 36, wherein the selected anatomical structure is the eye, and the measure of temperature information is the mean, the mean being based on maximum temperatures of the eye.

38. The method according to claim 1, wherein the selected anatomical structure is selected from a lateral eye, a frontal nose, a frontal ear or a posterior surface of a mammary gland.

39. A method for the detection of inflammation of a selected anatomical structure of an animal, comprising:
- (a) scanning the selected anatomical structure of the animal with an infrared camera to obtain an infrared thermographic image of the selected anatomical structure of the animal;
- (b) processing the image to provide a mean temperature for only a portion of the infrared thermographic image representing the selected anatomical structure;
- (c) comparing the mean temperature from step (b) to a mean temperature of only the same selected anatomical structure of either the same animal or a population of animals of the same species obtained from only a portion of one or more infrared thermographic images representing the same selected anatomical structure taken when there was no inflammation of the same selected anatomical structure; and
- (d) either detecting early or subclinical inflammation of the anatomical structure of the animal if there is a change in the mean temperature of less than 1° C., or detecting late stage development of inflammation of the anatomical structure of the animal if there is a change in the mean temperature of greater than 1° C.

40. A method for detecting infection of an animal, comprising the steps of:
- (a) scanning a selected anatomical structure selected from a tissue, a joint, a lateral side or a dorsal side of the animal with an infrared camera to obtain an infrared thermographic image of the selected anatomical structure of the animal;
- (b) processing the image to provide a measure of temperature information selected from a measure of central tendency, a measure of dispersion, or total temperature for only a portion of the image representing the selected anatomical structure;
- (c) comparing the measure of the temperature information to a predetermined value, the predetermined value being a measure of central tendency, a measure of dispersion, or total temperature obtained from only a portion of one or more infrared thermographic images representing the same selected anatomical structure of either the same animal pre-infection or the same selected anatomical structure of a population of uninfected animals of the same species; and
- (d) detecting subclinical, early or clinical infection of the animal if the measure of the temperature information is greater than the predetermined value by at least a predetermined amount.

\* \* \* \* \*